United States Patent

Haase et al.

(10) Patent No.: US 7,374,749 B2
(45) Date of Patent: May 20, 2008

(54) AMINO SUBSTITUTED HYDROXYPHENYL BENZOPHENONE DERIVATIVES

(75) Inventors: Jürg Haase, Bettingen (CH); Thomas Ehlis, Freiburg (DE); Elek Borsos, Birsfelden (CH); Stefan Müller, Weil am Rhein (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 94 days.

(21) Appl. No.: 10/537,940

(22) PCT Filed: Dec. 3, 2003

(86) PCT No.: PCT/EP03/50937

§ 371 (c)(1),
(2), (4) Date: Jun. 7, 2005

(87) PCT Pub. No.: WO2004/052837

PCT Pub. Date: Jun. 24, 2004

(65) Prior Publication Data

US 2006/0018846 A1   Jan. 26, 2006

(30) Foreign Application Priority Data

Dec. 12, 2002 (EP) .................. 02406093
Jun. 25, 2003 (CH) .................... 1113/03
Jul. 25, 2003 (EP) .................. 03102297

(51) Int. Cl.
A61K 8/44   (2006.01)
A61K 8/49   (2006.01)
C07D 277/66 (2006.01)
C07D 313/12 (2006.01)
C07C 233/73 (2006.01)
C07C 233/69 (2006.01)
C07C 233/78 (2006.01)
C07C 229/52 (2006.01)

(52) U.S. Cl. .......... 424/60; 424/59; 548/180; 549/268; 560/19; 564/168

(58) Field of Classification Search .......... 548/180; 564/168; 549/268
See application file for complete search history.

(56) References Cited

U.S. PATENT DOCUMENTS 6,409,995 B1    6/2002  Habeck et al. .............. 424/59
6,488,915 B1 * 12/2002  Heidenfelder et al. ....... 424/59

* cited by examiner

Primary Examiner—Rebecca Anderson
Assistant Examiner—Jason M Nolan
(74) Attorney, Agent, or Firm—Mervin G. Wood

(57) ABSTRACT

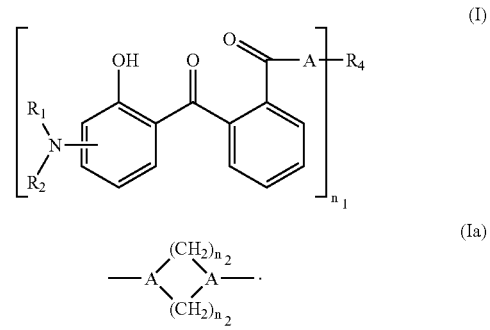

Described are amino substituted hydroxyphenyl benzophenone derivatives of formula (I), wherein $R_1$, and $R_2$ independently from each other are; $C_1$-$C_{20}$alkyl; $C_2$-$C_{20}$-alkenyl; $C_3$-$C_{10}$cycloalkyl; $C_3$-$C_{10}$cycloalkenyl; or $R_1$, and $R_2$ together with the linking nitrogen atom form a 5- or 6-membered heterocyclic ring; $n_1$ is a number from 1 to 4; when $n_1=1$, $R_3$ is a saturated or unsaturated heterocyclic radical; hydroxy-$C_1$-$C_5$alkyl; cyclohexyl optionally substituted with one or more $C_1$-$C_5$alkyl; phenyl optionally substituted with a heterocyclic radical, aminocarbonyl or $C_1$-$C_5$alkylcarboxy; when $n_1$ is 2, $R_3$ is an alkylene-, cycloalkylene- or alkenylene radical which is optionally substituted by a carbonyl- or carboxy group; o $R_3$ together with A forms a bivalent radical of the formula (Ia), wherein $n_2$ is a number from 1 to 3; when $n_1$ is 3, $R_3$ is an alkanetriyl radical; when $n_1$ is 4, $R_3$ is an alkanetetrayl radical; A is —O—; or —N($R_5$)—; and $R_5$ is hydrogen; $C_1$-$C_5$alkyl; or hydroxy-$C_1$-$C_5$alkyl. The compounds are useful as UV filters in sunscreen applications.

26 Claims, No Drawings

AMINO SUBSTITUTED HYDROXYPHENYL BENZOPHENONE DERIVATIVES

The present invention relates to amino substituted hydroxyphenyl benzophenone derivatives, the process for the preparation of these compounds, the use of these UV absorbers, preferably for the protection of human and animal hairs and from the damage of UV radiation as well as cosmetic compositions comprising these compounds.

The new compounds correspond to the formula

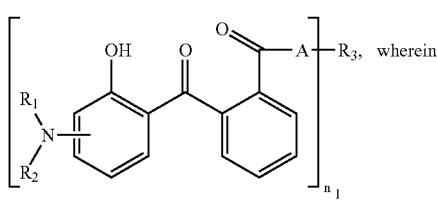

$R_1$ and $R_2$ independently from each other are; $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;
$n_1$ is a number from 1 to 4;
when $n_1=1$,
$R_3$ is a saturated or unsaturated heterocyclic radical; hydroxy-$C_1$-$C_5$alkyl; cyclohexyl optionally substituted with one or more $C_1$-$C_5$alkyl; phenyl optionally substituted with a heterocyclic radical, aminocarbonyl or $C_1$-$C_5$alkylcarboxy;
when $n_1$ is 2,
$R_3$ is an alkylene-, cycloalkylene, alkenylene or phenylene radical which is optionally substituted by a carbonyl- or carboxy group; a radical of formula *—$CH_2$—$C\equiv C$—$CH_2$—* or $R_3$ together with A forms a bivalent radical of the formula (1a)

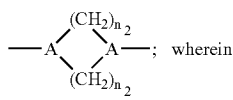

$n_2$ is a number from 1 to 3;
when $n_1$ is 3,
$R_3$ is an alkantriyl radical;
when $n_1$ is 4,
$R_3$ is an alkantetrayl radical;
A is —O—; or —N($R_5$)—; and
$R_5$ is hydrogen; $C_1$-$C_5$alkyl; or hydroxy-$C_1$-$C_5$alkyl.

$C_1$-$C_{20}$Alkyl denotes a linear or branched, unsubstituted or substituted alkyl group such as, for example, methyl, ethyl, propyl, isopropyl, n-butyl, n-hexyl, cyclohexyl, n-decyl, n-dodecyl, n-octadecyl, eicosyl, methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-2,4-di-tert-amylphenoxy)-propyl, ethoxycarbonylmethyl-2-(2-hydroxyethoxy)ethyl or 2-furylethyl.

$C_2$-$C_{20}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_3$-$C_{10}$cycloalkenyl is for example cyclopropyl, cyclobutyl, cyclopentyl, cycloheptyl, cyclooctyl, cyclononyl or cyclodecyl and preferably cyclohexyl. These radicals may be substituted, for example by one or more oder equal or different $C_1$-$C_4$alkyl radicals, preferably by methyl, and/or hydroxy. If cycloalkyl radicals are substituted by one or more radicals, they are preferably substituted by one, two or four, preferably by one or two equal or radicals.

$C_3$-$C_{10}$cycloalkenyl is for example cyclopropenyl, cyclobutenyl, cyclopentenyl, cycloheptenyl, cyclooctenyl, cyclononenyl or cyclodecenyl and preferably cyclohexenyl. These radicals may be substituted with one or more equal or different $C_1$-$C_4$alkyl radical, preferably with methyl, and/or hydroxy. If cycloalkenyl radicals are substituted with one or more radicals they are preferably substituted with one, two, three or four, preferably with one or two equal or different radicals.

Hydroxy substituted $C_1$-$C_5$alkyl groups are for example hydroxymethyl, hydroxyethyl, hydroxypropyl, hydroxybutyl or hydroxypentyl.

An alklyene radical is preferably a $C_1$-$C_{12}$alkylene radical, like for example methylene, ethylene, propylene, butylene, hexylene or octylene.

The alklyene radicals may optionally be substituted by one or more $C_1$-$C_5$alkyl radicals.

If $R_1$ and $R_2$ are heterocyclic radicals, these comprise one, two, three or four equal or different ring hetero atoms. Special preference is given to heterocycles which contain one, two or three, especially one or two, identical or different hetero atoms. The heterocycles may be mono- or polycyclic, for example mono-, bi- or tri-cyclic. They are preferably mono- or bi-cyclic, especially monocyclic. The rings preferably contain 5, 6 or 7 ring members. Examples of monocyclic and bicyclic heterocyclic systems from which radicals occurring in the compounds of formula (1) or (2) may be derived are, for example, pyrrole, furan, thiophene, imidazole, pyrazole, 1,2,3-triazole, 1,2,4-triazole, pyridine, pyridazine, pyrimidine, pyrazine, pyran, thiopyran, 1,4-dioxane, 1,2-oxazine, 1,3-oxazine, 1,4-oxazine, indole, benzothiophene, benzofuran, pyrrolidine, piperidine, piperazine, morpholine and thiomorpholine.

Preference is given to compounds of formula (1), wherein $R_1$ and $R_2$ independently from each other are hydrogen; $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;
$n_1$ is a number from 1 to 4;
wenn $n_1$ is 1,
$R_3$ is a saturated or unsaturated heterocyclic radical; hydroxy-$C_1$-$C_5$alkyl; Cyclohexyl substituted with one or more $C_1$-$C_5$alkyl;
wenn $n_1$ is 2,
$R_3$ is an alkylene-, cycloalkylene- or alkenylene radical which is optionally interrupted by a carbonyl- or carboxy group;
wenn $n_1$ is 3,
$R_3$ is an alkantriyl radical;
wenn $n_1$ is 4,
$R_3$ is an alkanetetrayl radical;
A is —O—; or —N($R_5$)—; and
$R_5$ is hydrogen; $C_1$-$C_5$alkyl; or hydroxy-$C_1$-$C_5$alkyl.

Of preferred interest are compounds of formula (1), wherein
$R_1$ and $R_2$ are $C_1$-$C_{20}$alkyl, preferably $C_1$-$C_5$alkyl; and most preferably ethyl.

Preferably $R_1$ and $R_2$ in formula (1) have the same definition.

If in formula (1) $n_1$ is 1, compounds are preferred, wherein $R_3$ is a saturated or unsaturated heterocyclic radical, most preferably a saturated heterocyclic radical.

Among these compounds are those preferred, wherein $R_3$ is a monocyclic radical of 5, 6 or 7 ring members with one or more heteroatoms, preferably wherein $R_3$ is morphonlinyl; piperazinyl; piperidyl; pyrazolidinyl; imadazolidinyl; or pyrrolidinyl.

When $n_1$ is 1 further compounds of formula (1) are of interest wherein $R_3$ is an unsaturated heterocyclic radical, preferably a polycyclic radical.

Most preferred are compounds of formula (1), wherein $R_3$ is a radical of formula (1a)

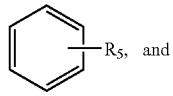

$R_5$ is polycyclic heteroaromatic radical with one or 2 heteroatoms.

Of preferred interest are compounds of formula (1), wherein $R_3$ is a radical of formula (1b)

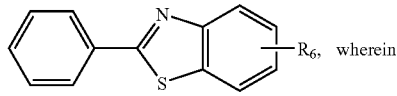

$R_6$ is hydrogen; or $C_1$-$C_5$alkyl.

If $n_1$ is 2, $R_3$ is preferably a $C_1$-$C_{12}$alkylene radical, most preferably a $C_2$-$C_6$alkylene radical.

Mostly preferred are compounds of formula (1), wherein $R_3$ is a radical of formula

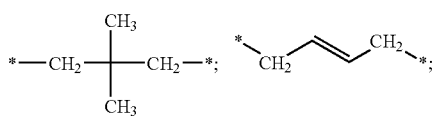

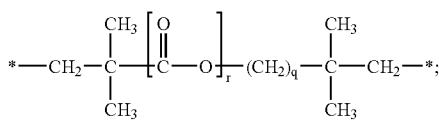

r is 0 or 1; and q=is a number from 0 to 5.

If in formula (1) $n_1$ is 3.

$R_3$ is preferably a radical of formula

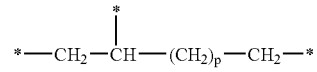

(1c)

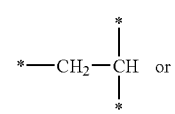

(1d)

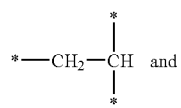

(1e)

p is a number from 0 to 3.

$R_1$, $R_2$ and A are defined as in formula (1).

If in formula (1) $n_1$ is 4, $R_3$ is a radical of formula

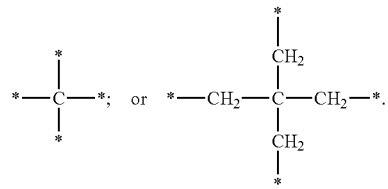

$R_1$, $R_2$ and A are defined as in formula (1).

Preferred compounds of the present invention correspond to formula

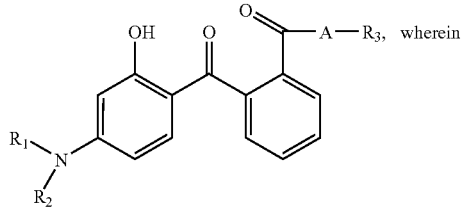

(2)

$R_1$ and $R_2$ independently from each other are hydrogen; or $C_1$-$C_5$alkyl;

A is —NH; or —O—; and $R_3$ is a saturated or unsaturated heterocyclic radical.

Furthermore compounds of the present invention are preferred which correspond to formula

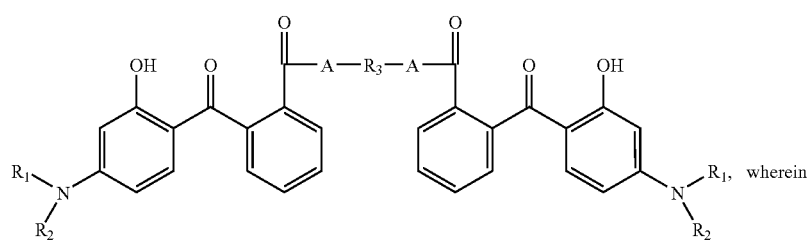
(3)
$R_1$ and $R_2$ independently from each other are hydrogen; or
$C_1$-$C_5$alkyl;
A is —NH; or —O—; and
$R_3$ is a $C_1$-$C_{12}$alkylene radical.
Preferred are also compounds of formula
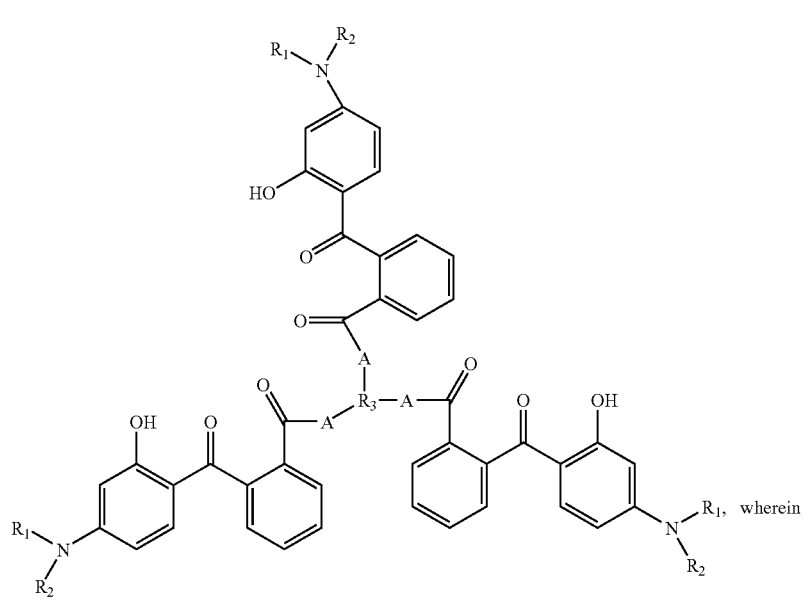
(4)
$R_1$ and $R_2$ independently from each other are hydrogen; or
$C_1$-$C_5$alkyl;
A is —NH; or —O—;
$R_3$ is
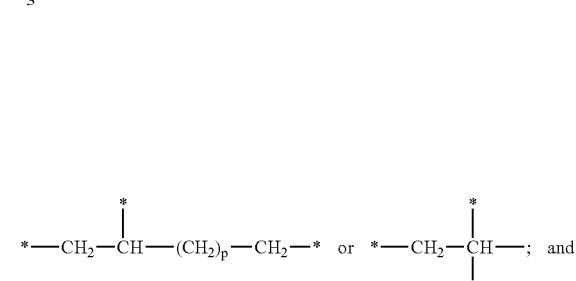
p is a number from 0 to 3.
Furthermore, compounds of formula
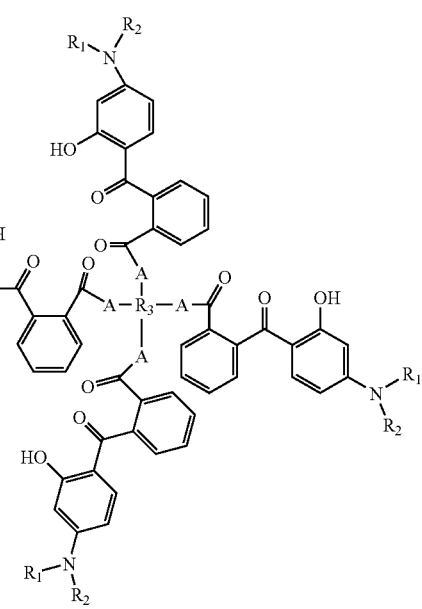
(5)

are preferred, wherein
R₃ is a radical of formula
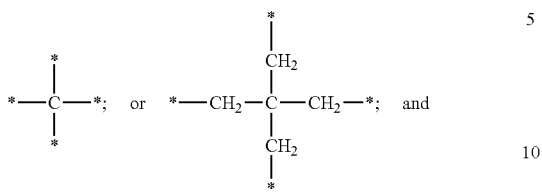
R₁, R₂ and A are defined as in formula (1).
Exemplified compounds of the present invention are of formulae
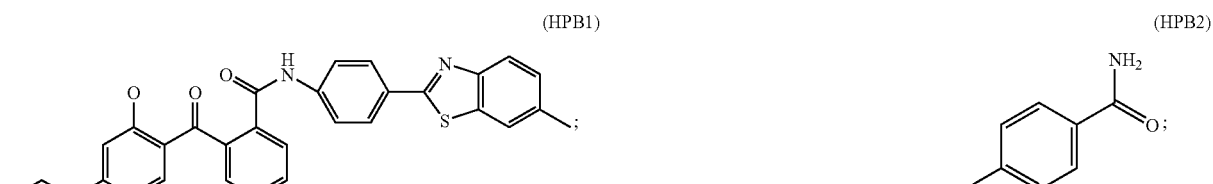
(HPB1)
(HPB2)
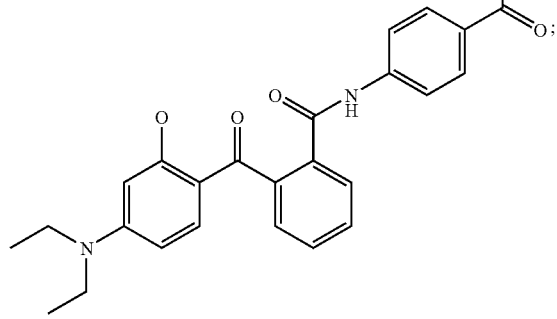
(HPB3)
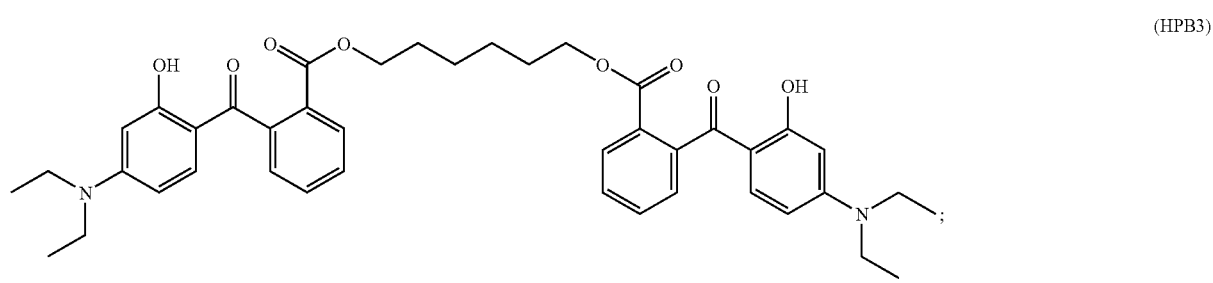
(HPB4)
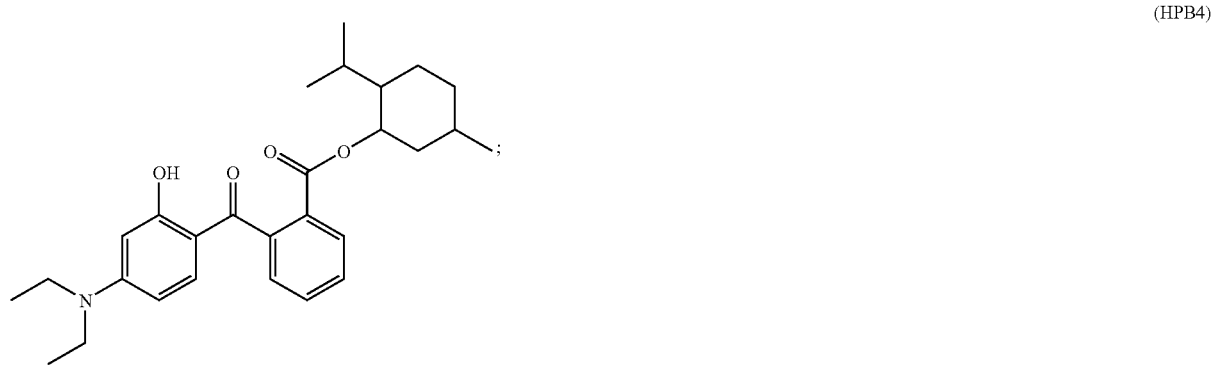

-continued
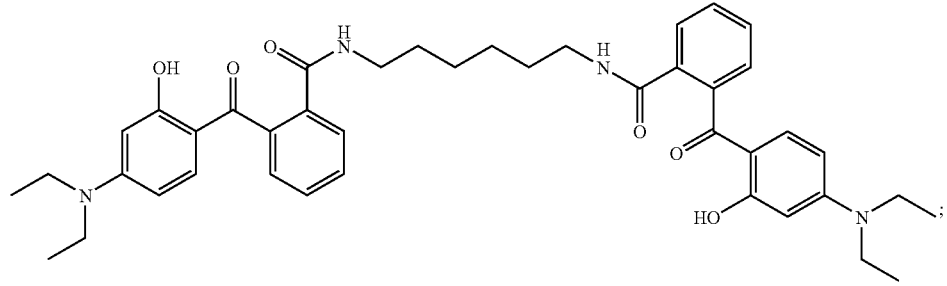
(HPB5)
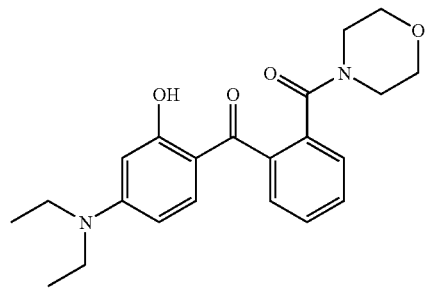
(HPB6)
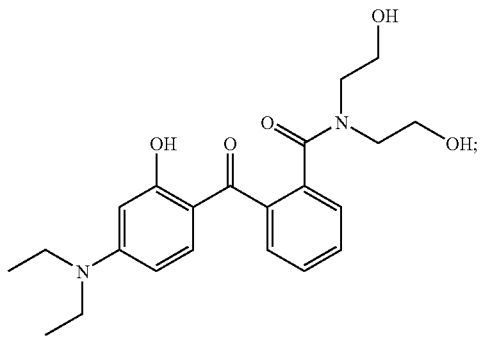
(HPB7)
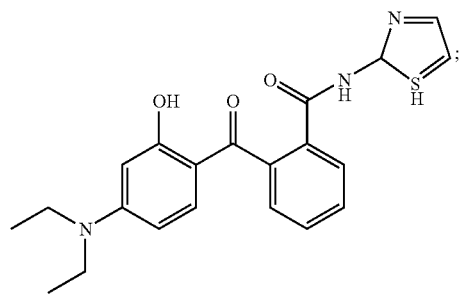
(HPB8)
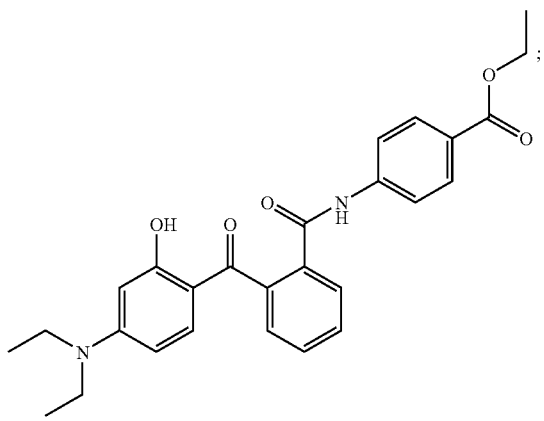
(HPB9)
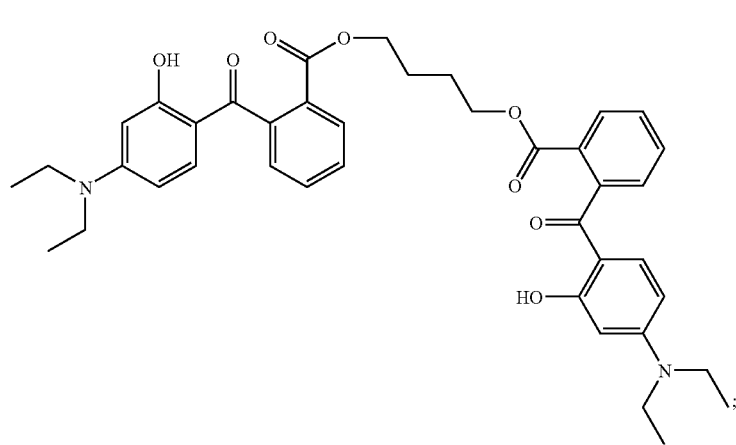
(HPB10)

-continued
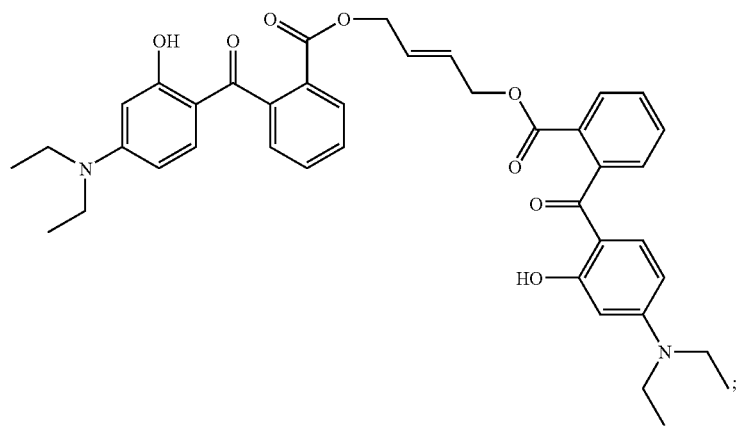
(HPB11)
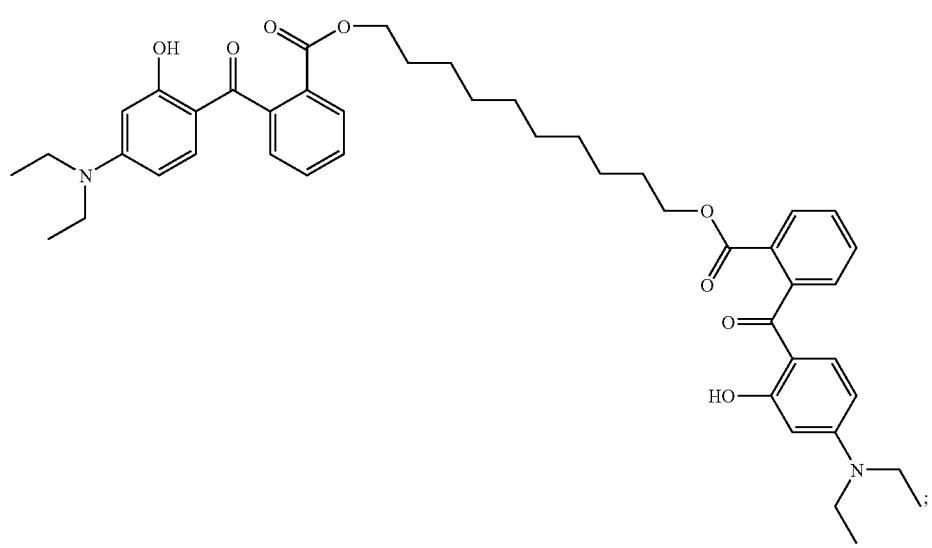
(HPB12)
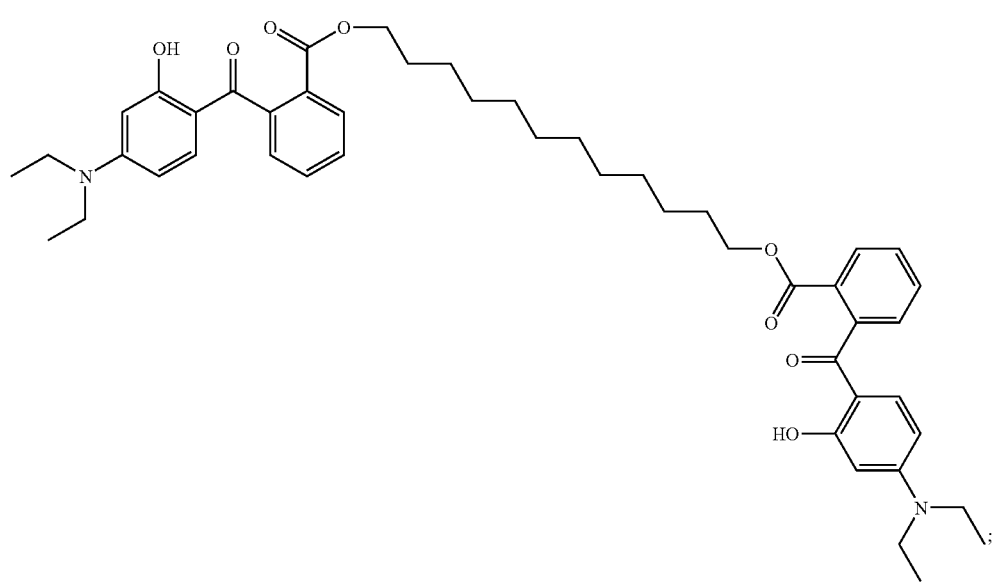
(HPB13)

-continued
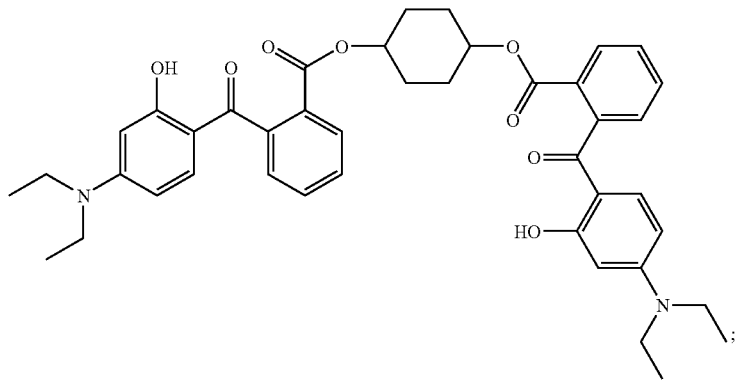
(HPB14)
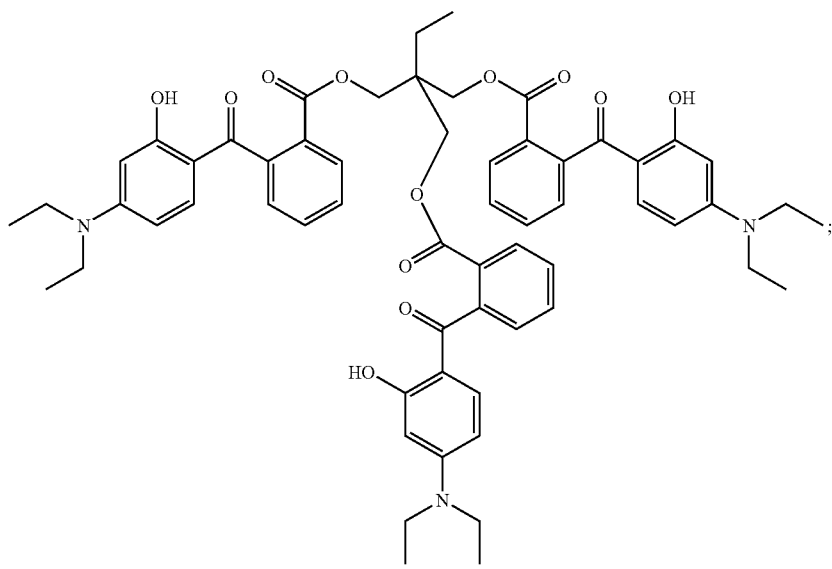
(HPB15)
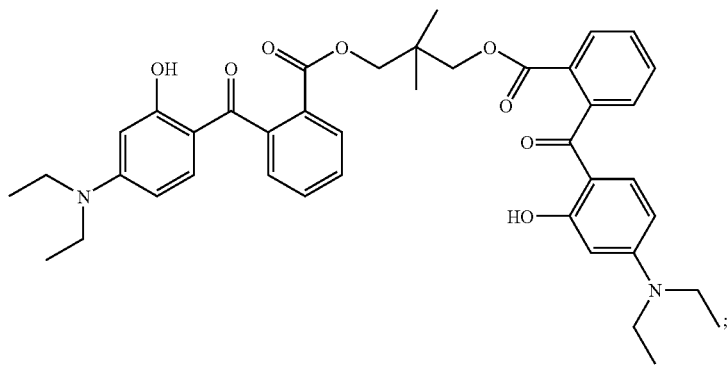
(HPB16)
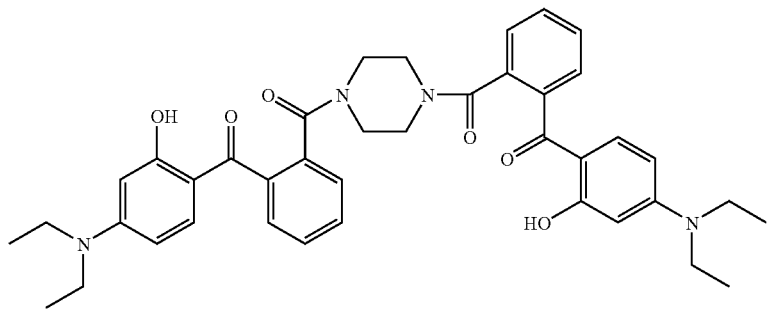
(HPB17)

-continued
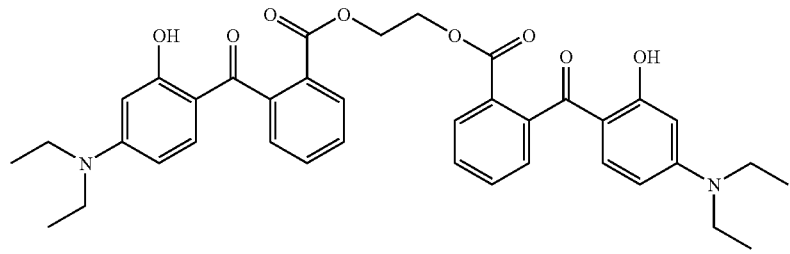
(HPB18)
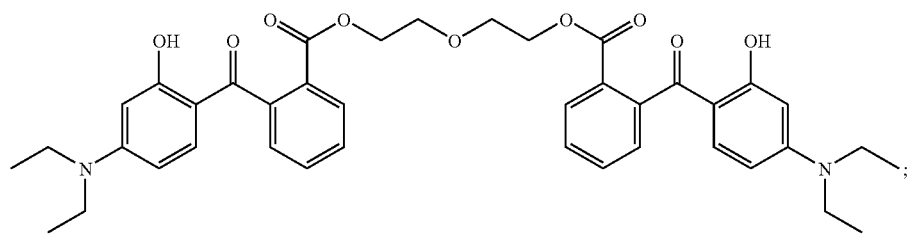
(HPB20)
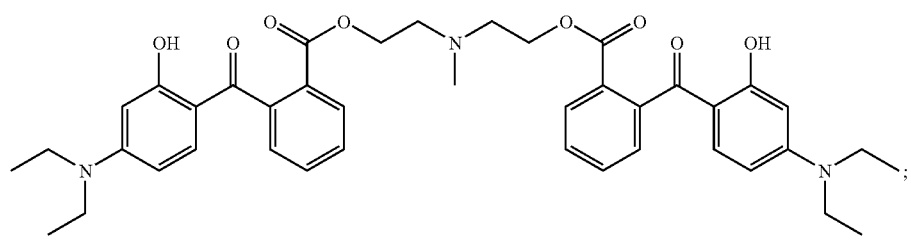
(HPB21)
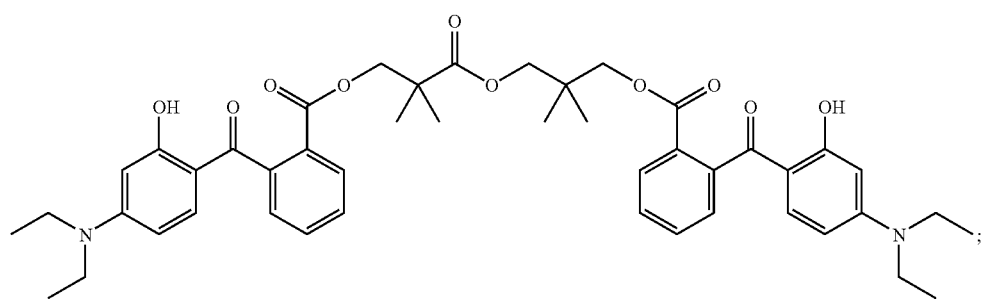
(HPB22)

-continued
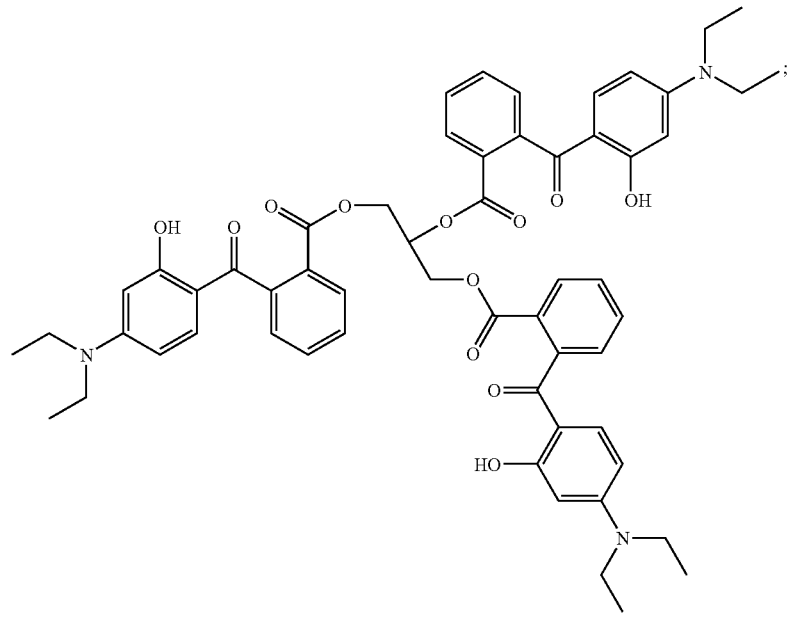
(HPB23)
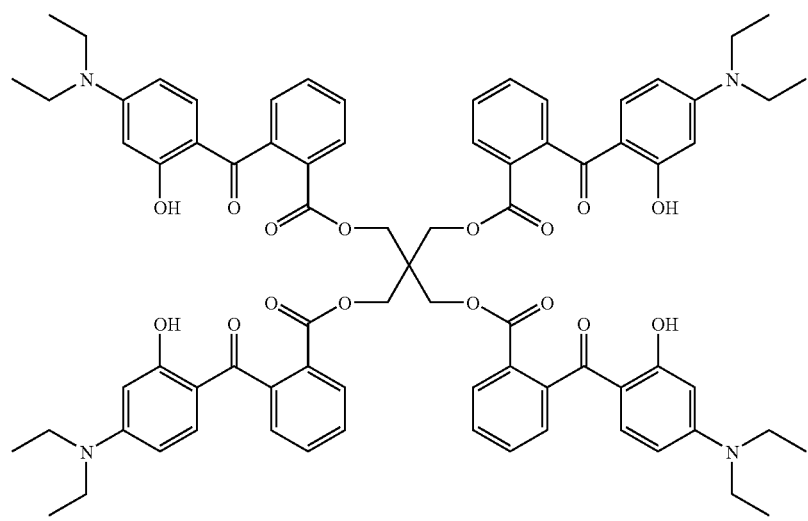
(HPB24)
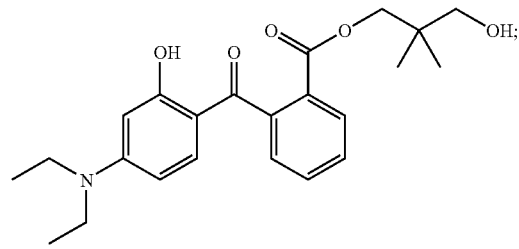
(HPB25)
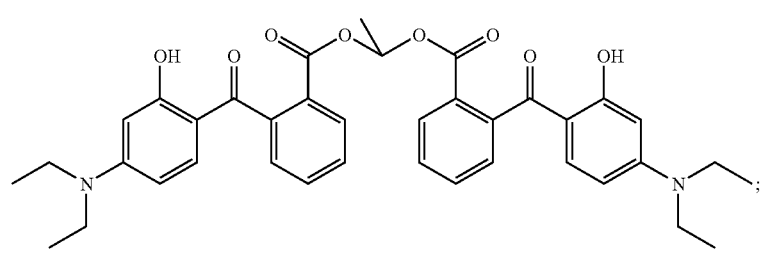
(HPB26)

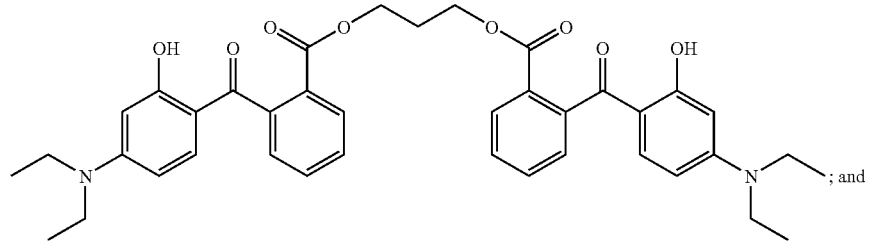
(HPB27)

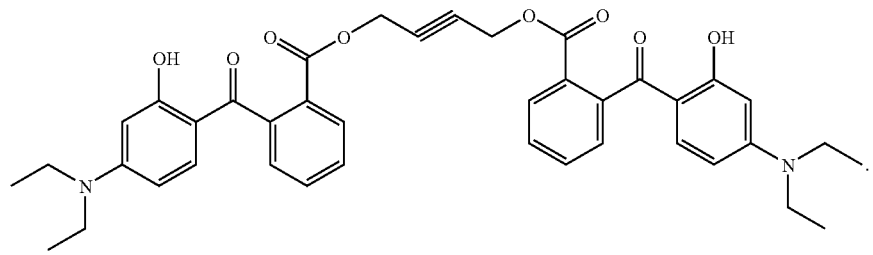
(HPB28)

The compounds of formula (1) may be prepared according to known methods as described for example in EP-1,046,391.

Preferably, the compounds formula (1) are prepared by (a) dehydratisation of formula (6a)

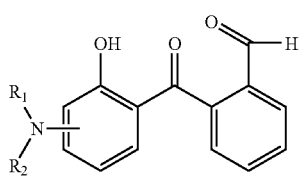

to the compound of formula

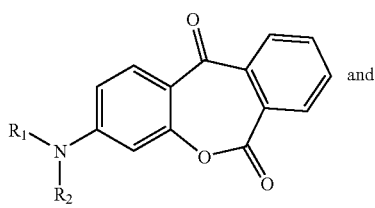
(6b)

(b) reacting the obtained anhydride with the compound (4c$_1$) H—N(R$_4$)—R$_3$ or H—O—R$_3$ to the compound of formula

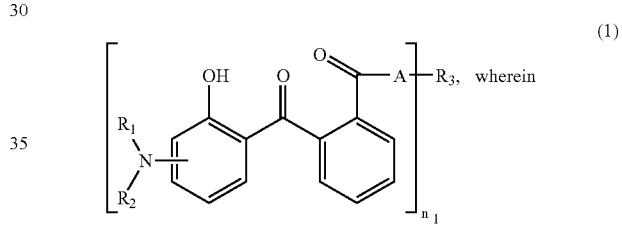

(1)

R$_1$ and R$_2$ independently from each other are hydrogen; C$_1$-C$_{20}$alkyl; C$_2$-C$_{20}$alkenyl; C$_3$-C$_{10}$cycloalkyl; C$_3$-C$_{10}$cycloalkenyl; or R$_1$ and R$_2$ together with the linking nitrogen atom form a 5- or 6-membered heterocyclic ring;

n$_1$ is 1 to 4;
when n$_1$ is 1.
R$_3$ is hydrogen; C$_1$-C$_{20}$alkyl; hydroxy-C$_{1-5}$alkyl; C$_2$-C$_{20}$alkenyl; C$_3$-C$_{10}$Cyclohexyl with is not substituted or substituted by one or more C$_1$-C$_5$alkyl; (Y—O)$_p$Z; C$_6$-C$_{10}$aryl; or a saturated or unsaturated heterocyclic radical;
Y is C$_1$-C$_{12}$alkylene;
Z is C$_1$-C$_5$alkyl;
p is a number from 1 to 20;
if n$_1$ is 2
R$_3$ is an alkylene-, cycloalkylene- or alkenylene radical which is optionally interrupted by carbonyl- or carboxy group;
if n$_1$ is 3,
R$_3$ is an alkantriyl radical;
if n$_1$ is 4,
R$_3$ is a alkantetrayl radical;
A is —O—; or —N(R$_5$);
R$_5$ is hydrogen; C$_1$-C$_5$alkyl; or hydroxy-C$_1$-C$_5$alkyl; and
R$_5$ is hydrogen; C$_1$-C$_5$alkyl; or hydroxy-C$_1$-C$_5$alkyl.

The process for the preparation is a further object of the present invention.

Preferably compounds of formula

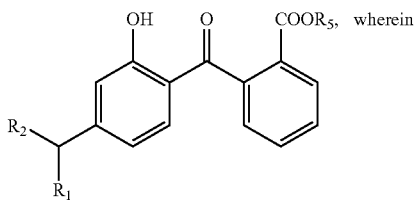
(7)

$R_1$ and $R_2$ independently from each other are $C_1$-$C_{12}$alkyl; and
$R_5$ is hydrogen; $C_1$-$C_{12}$alklyl; or $C_3$-$C_6$cycloalkyl;
can be obtained according to the process of the present invention.

The reaction is usually carried out at a temperature from 25 to 200° C., preferably at room temperature. Generally a solvent is not necessary for this reaction step. If a solvent is used however, preferably the solvents as used in the working examples are preferred.

The compounds of formula (1) may be easily recrystallized as x-HCl-salts.

The intermediates of formula

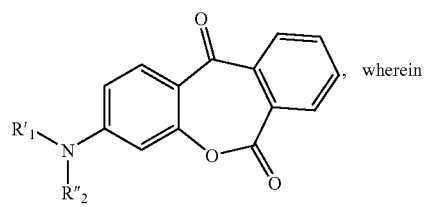
(6b')
, wherein $R_1'$ and $R_2''$ independently from each other are hydrogen; $C_1$-$C_{20}$alkyl; $C_2$-$C_{20}$-alkenyl; $C_3$-$C_{10}$cycloalkyl; $C_3$-$C_{10}$cycloalkenyl; or $R_1$ and $R_2$ together with the lining nitrogen atom form a 5- or 6-membered heterocyclic ring;

are compounds not known from the prior art.

They represent starting compounds for the preparation of organic UV filters.

The compounds of formula (6b') are a further object of the present invention.

The compounds of formula (1) are suitable especially as UV filters, that is to say for the protection of organic materials that are sensitive to ultraviolet light, especially human and animal skin and hair, against the action of UV radiation. Such compounds are accordingly suitable as light-protective agents in cosmetic, pharmaceutical and veterinary medicine preparations.

A further object of the present invention is therefore a cosmetic preparation comprising at least one of the compounds of formula (1) together with cosmetically acceptable carriers or adjuvants.

The UV absorbers according to the present invention can be used either in the dissolved state (soluble organic filters, solubilised organic filters) or in the micronised state (nanoscalar organic filters, particulate organic filters, UV-absorber pigments).

Any known process suitable for the preparation of microparticles can be used for the preparation of the micronised UV absorbers, for example:

wet-milling (low-viscosity micronisation process for pumpable dispersions), with a hard grinding medium, for example zirconium silicate balls in a ball mill, and a protective surfactant or a protective polymer in water or in a suitable organic solvent;

wet-kneading (high-viscosity micronisation process for non-pumpable pastes) using a continuous or discontinuous (batch) kneader. For a wet-kneading process, a solvent (water or cosmetically acceptable oils), a grinding aid (surfactant, emulsifier) and a polymeric grinding aid may be used.

Both processes may be used preferably.

spray-drying from a suitable solvent, for example aqueous suspensions or suspensions containing organic solvents, or true solutions in water, ethanol, dichloroethane, toluene or N-methylpyrrolidone etc., by expansion according to the RESS process (Rapid Expansion of Supercritical Solutions) of supercritical fluids (e.g. $CO_2$) in which the UV filter or filters is/are dissolved, or the expansion of liquid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As milling apparatus for the preparation of the micronised organic UV absorbers there may be used, for example, a jet mill, ball mill, vibratory mill or hammer mill, preferably a high-speed mixing mill. Even more preferable mills are modern ball mills; manufacturers of these types of mill are, for example, Netzsch (LMZ mill), Drais (DCP-Viscoflow or Cosmo), Bühler AG (centrifugal mills) or Bachhofer. The grinding is preferably carried out with a grinding aid.

Examples of kneading apparatus for the preparation of the micronised organic UV absorbers are typical sigma-blade batch kneaders but also serial batch kneaders (IKA-Werke) or continuous kneaders (Continua from Werner und Pfleiderer).

Useful low molecular weight grinding aids for all the above micronisation processes are dispersing agents and surfactants and emulsifiers as disclosed below in the sections entitled "Emulsifiers", "Surfactants" and "Fatty alcohols".

Useful polymeric grinding aids for water dispersion are cosmetically acceptable water-soluble polymers with Mn>500 g/mol, for example: acrylates (Salcare types), modified or non-modified polysaccharides, polyglucosides or xanthan gum. Furthermore an alkylated vinylpyrrolidone polymer, a vinylpyrrolidone/vinyl acetate copolymer, an acyl glutamate, an alkyl polyglucoside, Ceteareth-25 or a phospholipid may be used. Oil dispersions may comprise cosmetically acceptable waxy polymers or natural waxes as polymeric grinding aid to adjust the viscosity during and after processing. Examples of other useful polymeric grinding aids are disclosed below in the section entitled "Polymers".

Useful solvents are water, brine, (poly-)ethylene glycol, glycerol or cosmetically acceptable oils. Other useful solvents are disclosed below in the sections entitled "Esters of fatty acids", "Natural and synthetic triglycerides, including glyceryl esters and derivatives", "Pearlescent waxes", "Hydrocarbon oils" and "Silicones or siloxanes".

The micronised UV absorbers so obtained usually have an average particle size from 0.02 to 2 micrometres, preferably from 0.03 to 1.5 micrometres and more especially from 0.05 to 1.0 micrometres.

A further object of the present invention is a UV absorber dispersion, comprising
(a) a micronised UV absorber of formula

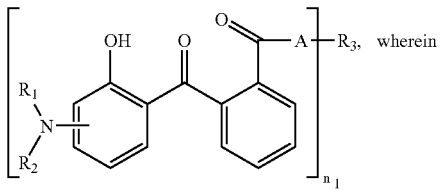

$R_1$ and $R_2$ independently from each other are hydrogen; $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;

when $n_1$ is 1, $R_3$ is hydrogen; $C_1$-$C_{20}$alkyl; hydroxy-$C_1$-$C_5$alkyl; $C_2$-$C_{20}$alkenyl; not substituted or with one or more $C_1$-$C_5$alkyl substituted $C_3$-$C_{10}$cyclohexyl; $(Y\text{---}O)_pZ$; $C_6$-$C_{10}$aryl; or a saturated or unsaturated heterocyclic radical;

Y $C_1$-$C_{12}$alkylen;

Z $C_1$-$C_5$alkyl;

p is a number from 1 to 20;

when $n_1$ is 2, $R_3$ is a alkylen-, cycloalkylen- or alkenylen-radical optionally interrupted by a carbonyl- or carboxy group;

if $n_1$ is, $R_3$ is an alkantriyl radical;

if $n_1$ is 4, $R_3$ is an alkantetrayl radical;

A is —O—; or —N($R_5$)—; and $R_5$ is hydrogen; $C_1$-$C_5$alkyl; or hydroxy-$C_1$-$C_5$alkyl;

$R_5$ is hydrogen; $C_1$-$C_5$alkyl; or hydroxy-$C_1$-$C_5$Alkyl;

Having a particle size from 0.02 to 2 µm, and (b) a suitable dispersing agent

The UV absorbers according to the present invention can also be used dry in powder form. For that purpose, the UV absorbers are subjected to known grinding methods, such as vacuum atomisation, countercurrent spray-drying etc. Such powders have a particle size of from 0.1 micrometers to 2 micrometers. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, an acrylate etc.

The UV absorbers according to the present invention can also be used in specific carriers for cosmetics, for example in solid lipid nanoparticles (SLN) or in inert sol-el microcapsules wherein the UV absorbers are encapsulated.

The cosmetic formulations or pharmaceutical compositions according to the present invention can also comprise one or more than one further UV filter.

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, for example octyl methoxycinnamate, salicylic acid isooctyl ester etc. The UV absorber can be used, for example, without further treatment, or in the micronised state, or in the form of a powder.

Cosmetic or pharmaceutical preparations contain from 0.05% to 40% by weight, based on the total weight of the composition, of one UV absorber or a mixture of UV absorbers.

Preference is given to the use of mixing ratios of the UV absorber of formula (1) according to the present invention and optional further light-protective agents of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably approximately 50:50. Such mixtures can be used, inter alia, to improve solubility or increase UV absorption.

The UV absorbers of formula (1) according to the present invention or combinations of UV filters are useful for protecting skin, hair and/or natural or artificial hair colour.

Suitable UV filter substances which can additionally be used with the UV absorbers according to the present invention are any UV-A and UV-B filter substances.

The cosmetic or pharmaceutical preparations may be, for example, creams, gels, lotions, alcoholic and aqueous/alcoholic solutions, emulsions, wax/fat compositions, stick preparations, powders or ointments. In addition to the above-mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions preparations according to the invention may also comprise one or one more additional compounds as described below, for example fatty alcohols, esters of fatty adds, natural or synthetic triglycerides, including glyceryl esters and derivatives Pearlescent waxes, Hydrocarbon oils, silicones or siloxanes (organo-substituted polysiloxanes), fluorinated or perfluorinated oils, emulsifiers, adjuvants and additives, uperfatting agents, surfactants, consistency regulators, thickeners and rheology modifiers, polymers, anti-dandruff agents, film formers, antioxidants, hydrotropic agents, preservatives and bacteria inhibiting agents, perfume oils, colorants, or polymeric beads or hollow spheres as SPF enhancers Cosmetic or Pharmaceutical Preparations Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of special interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

a$_1$) spontaneously emulsifying stock formulation, consisting of the UV absorber according to the invention, PEG-6-C$_{10}$oxoalcohol and sorbitan sesquioleate, to which water and any desired quaternary ammonium compound, for example 4% minkamidopropyl dimethyl-2-hydroxyethylammonium chloride or Quaternium 80, is added;

a$_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80, is added;

b) quat-doped solutions of the UV absorber according to the invention in butyl triglycol and tributyl citrate;

c) mixtures or solutions of the UV absorber according to the invention with n-alkylpyrrolidone.

Other typical ingredients in such formulations are preservatives, bactericides and bacteriostatic agents, perfumes, dyes, pigments, thickening agents, moisturising agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

Preparation of New Compounds

EXAMPLE 1

Preparation of 3-diethylamino-dibenzo-oxepin (DEDO)

62.7 g of the compound of formula

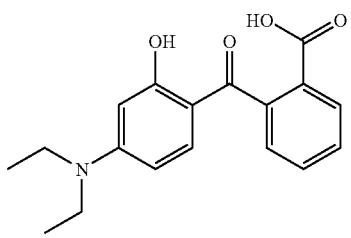
(101a)

are suspended in a reaction vessel at room temperature under stirring in 400 g acetic add ethyl ester. A solution of 44.4 g dicyclohexylcarbodiimid, dissolved in 200 g acetic add ethyl ester is mixed in this suspension. The temperature rises up to about 30° C. The suspension is stirred vigorously at room temperature during about 10 hours and filtered afterwards. After evaporation the pure product of formula

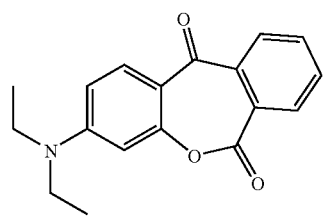
(101)

is obtained by crystallization from a mixture of acetic add ethyl ester (60 g)/cyclohexan (220 g) as yellow crystals.

| Yield: | 42 g |
|---|---|
| Fp: | 83.5° C. |

Analyses: C, H, N content corresponds to the theory values; H-NMR; C-NMR; MS confirms the oxepin structure.

Analogous to this procedure the compounds can be obtained by dehydratisation of BB-acid with acetic anhydride instead of dicyclohexyl carbodiimide.

EXAMPLE 2

Preparation of the Compound of Formula

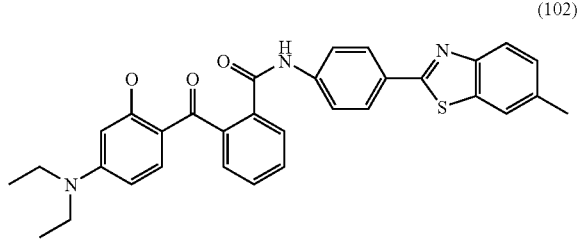
(102)

7.2 g of 2-(4-aminophenyl)-6-methyl-benzothiazol are suspended in 60 ml diethylenglycol-dimethylether at room temperature. A solution of 10.6 g of the compound of formula (101), dissolved in 20 ml diethylenglycol-dimethylether, are added under stirring and the reaction mass is heated up 90° C. After a reaction time of 4 hours the reaction mass is cooled down to room temperature and the raw product is filtered off. The pure compound is obtained by extraction of the raw product with ethanol.

| Yield: | 7.3 g beige powder |
|---|---|
| Fp: | 225° C. |

C=71.6%; H=5.2%; N=7.8%; S=5.96%
All values correspond with theory.

UV Spectrum in Dioxan;

1. Maximum at 336 nm e=57318
2. Maximum at 360 nm e=49032

EXAMPLE 3

Preparation of a Dispersion with Active Content of 38%

In Dispermat LC equiped with 19.3 g grinding pearls ER 120 S, 0.3-0.4 mm 3.49 of the compound of formula (102)

0.3 g Arlacel P 135 and 5.3 g Crodamol AB are grinded during 4.5 hours. A very fine grinded dispersion is obtained which has a SPF value of 16.4.

This dispersion covers very good a broad UV-rang (320-380 nm)

EXAMPLE 4

Preparation of the Compound of Formula (103)

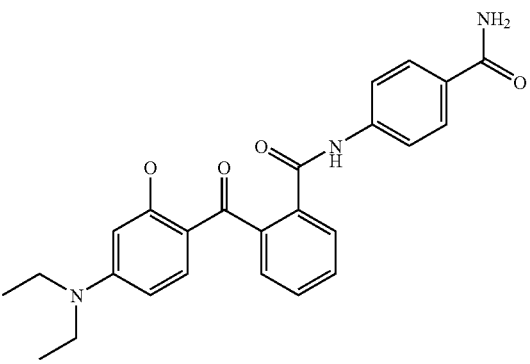

6 g of the compound of formula (101) are dissolved in 40 ml Dioxan. 2.5 g 4-aminobenzamide are added to this solution while stirring. After a reaction time of 2 hours at 85° C. dioxan is removed under vacuum and the residue is worked up by recrystallization from 2-methoxyethanol to the pure product.

| Yield: | 3 g white crystals |
|---|---|
| Fp | 254° C. |

Elemental analysis: C, H, N content corresponds to the theory.
UV-Spectrum in Dioxan:
Maximum at 358 nm; e=34848

EXAMPLE 5

Preparation of the Compound of Formula (104)

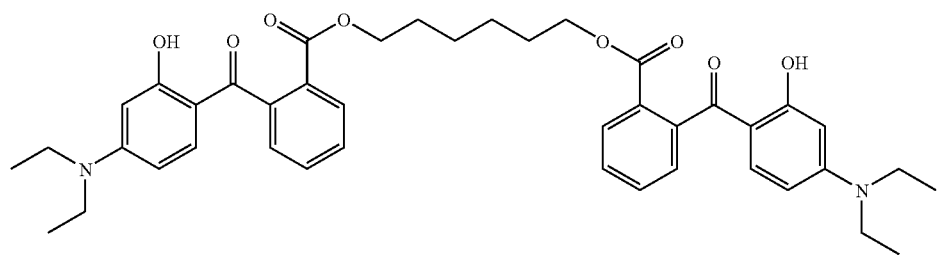

2.36 g 1,6-hexandiol, 6 g toluene and 11.8 g of the compound of formula (101) are stirred during 5 hours at 110° C.

Afterwards toluene is distilled off and the distilled residue is recrystallized from acetone.

| Yield: | 7.2 g white crystals |
|---|---|
| Fp: | 148° C. |

EXAMPLE 6

Preparation of the Compound of Formula

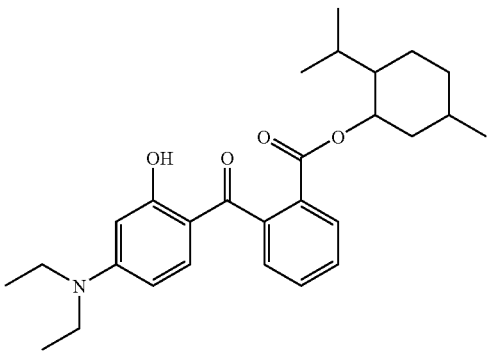

(105)

9.2 g of the compound of formula (101), 14.4 g of the racemic mixture of menthol, 18 ml of diethylenglycol-dimethylether, 0.1 g of 1.8-diazabicyclo(5.4.0)-undec-7-ene (1,5,5) are stirred at 100° C. during 2 hours. Then the solvent is resolved in vacuum and the residue separated with column chromatographic methods (Kieselgel 60/Toluene-acetic acid ester 8:2).

Yield: 12.8 g of a glassy non-crystalline mass

Analyses: C/H/N=74.5%/18.4%/3.04% corresponding to the theory.

UV Spectrum in Dioxan:
Maximum at 351 nm; e=38565

EXAMPLE 7

Preparation of the Compound of Formula

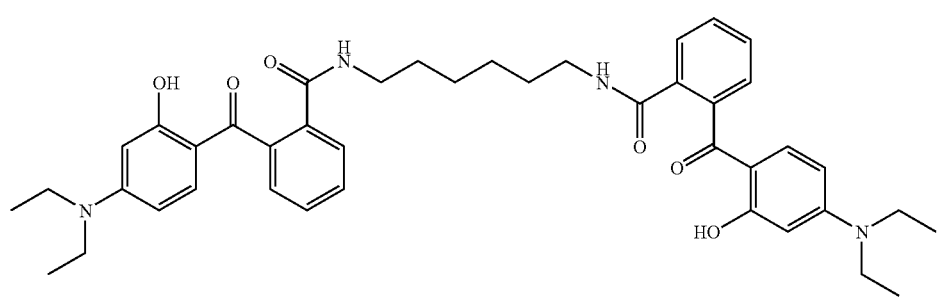

(106)

6 g of the compound of formula (101) are dissolved in 30 ml dioxan at room temperature. 1.16 g 1.6-diaminohexane, dissolved in 20 ml dioxan are added to this solution under stirring. Stirring of the reaction masse at room temperature is continued during 12 hours, then dioxan is removed in the vacuum and the raw product is recrystallized after extraction with water from methanol.

| Yield: | 4.2 g, yellow crystals |
|---|---|
| Fp: | 160° C. |

Elemental analysis corresponds to the theoretical values.

EXAMPLE 8

Preparation of the Compound of Formula (107)

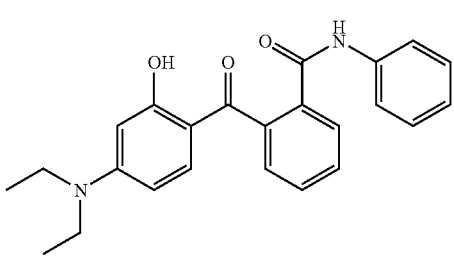

9 g of the compound of formula (101) and 8.4 g aniline are dissolved in 18 ml diethylenglycol-dimethylether. The reaction is warmed up to 70° C. and stirred at this temperature for 3 hours. After evaporation of the reaction mass in vacuum the pure product is obtained after recrystallization from methanol.

| Yield: | 6.2 g yellow crystals |
|---|---|
| Fp: | 152° C. |

UV Spectrum (in Dioxan)
Maximum at 359 nm; e=34724

EXAMPLE 9

Preparation of the Compound of (108)

7.4 g of the compound of formula (101) are dissolved in 25 ml dioxan. 3.3 g morpholine dissolved in 10 ml dioxan are stirred into this solution. The reaction mass is stirred during about 20 hours at room temperature, the reaction mixture is evaporated in vacuum and the pure product is recrystallized from acetic acid ethyl ester.

| Yield: | 7.5 g yellow crystals; |
|---|---|
| Fp. | 155° C. |

UV Spectrum (in Dioxan):
Maximum at 360 nm; e=37900

EXAMPLE 10

Preparation of the Compound of Formula

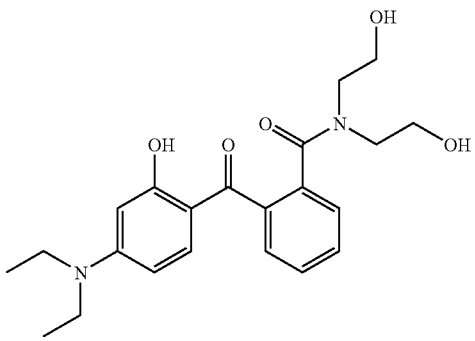
(109)

9 g of the compound of formula (101), 9.5 g diethanolamine, dissolved in 30 ml diehylenglycol-dimethylether are stirred at 85° C. during 3 hours. The reaction mass is narrowed in vacuum (0.03 mB/70° C.). The residue is extracted with ca. 250 ml water at 70° C. The pure compound recrystallizes from the aqueous phase after cooling down.

| Yield: | 2.1 g yellow crystals; |
|---|---|
| Fp. | 141° C. |

UV Spectrum (in Dioxan):
Maximum at 359 nm; e=35080

EXAMPLE 11

Preparation of the Compound of Formula

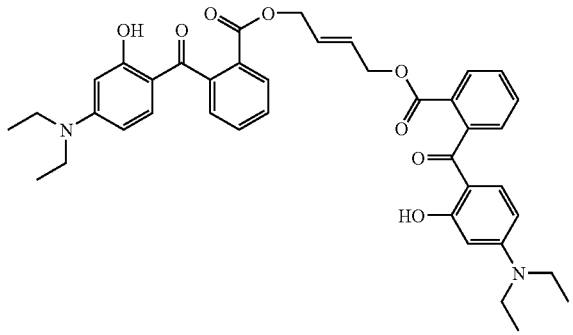
(110)

125.2 g 4-diethylamino-2-hydroxy-benzophenone-carbon acid (BB-add)
700 ml acetic acid ethyl ester,
38.8 g potassium carbonate; and
53.1 g acetanhydride
are stirred intensively during 16 hours at room temperature.
Then the reaction mixture is filtered off and the filtrate is evaporated to a weight of 157 g.

The anhydroform of the BB-acid (DEDO) recrystallizes from the vaporization residue

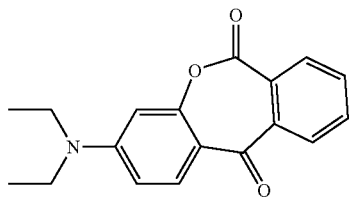
(101)

Yield: 99 g (yellow crystals, Fp=82° C.)
The crystals are dissolved in
18 g diethylenglykol-dimethylether,
14.6 g 2-Buten-1,4-diol is added and 1.1 g 4-dimethylamino-pyridine is added under stirring at 110° C. to the di-Ester (compound of formula (110)).
A quantitative yield is obtained.
The pure compound is obtained by column chromatographic methods—Kieselgel 60/diluent: Toluene acetic add ethyl ester/8:2.
The pure product in shred form is an amorphous yellow powder.
It has a good solubility for example in Finsolve TN (C 12-15 alkylbenzoate)>10%.
UV-Spectrum in Dioxan: Max. 351 nm, mol Ext. 65551

EXAMPLE 12

Preparation of the Compound of Formula

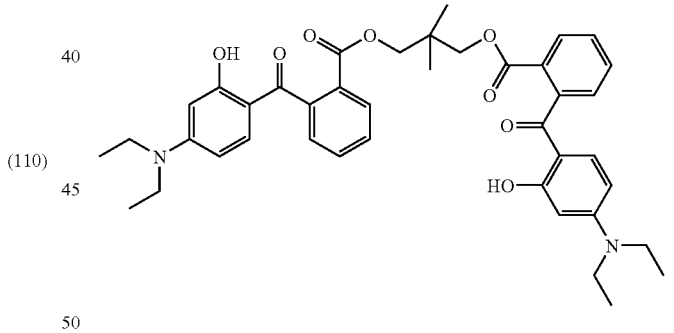
(111)

Analogous to example 11 17.3 g 2,2-Dimethyl-1,3-propandiol instead of 2-buten-1,4-diol are reacted with the anhydrous form of the BB-acid.
The working up of the raw product can be carried out according to the methods as described above.
The obtained compound is an amorphous, yellow powder
Solubility in Finsolve TN>30%
UV Spectrum in Ethanol: Max. 354 nm, mol. Ext. 65296

EXAMPLES 13 TO 23

Preparation of Further Hydroxyphenyl Benzophenone Derivatives

According to the method as described in Example 11 the following compounds can be prepared:

| Example | Compound of formula | Structure |
|---|---|---|
| 13 | 112 | 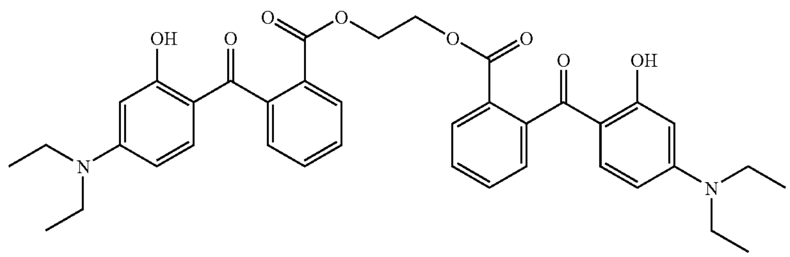 |
| 14 | 113 | 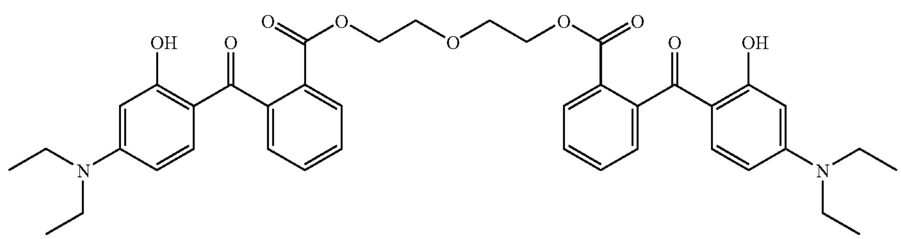 |
| 15 | 114 | 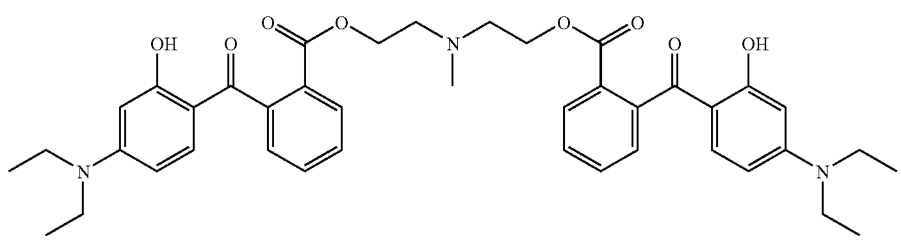 |
| 16 | 115 | 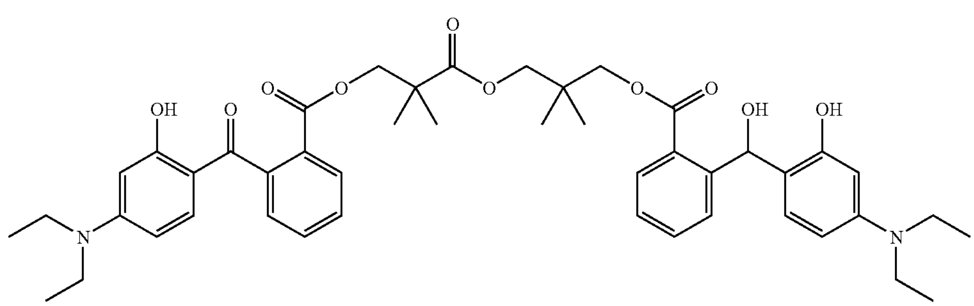 |

-continued
| Example | Compound of formula | Structure |
|---|---|---|
| 17 | 116 | 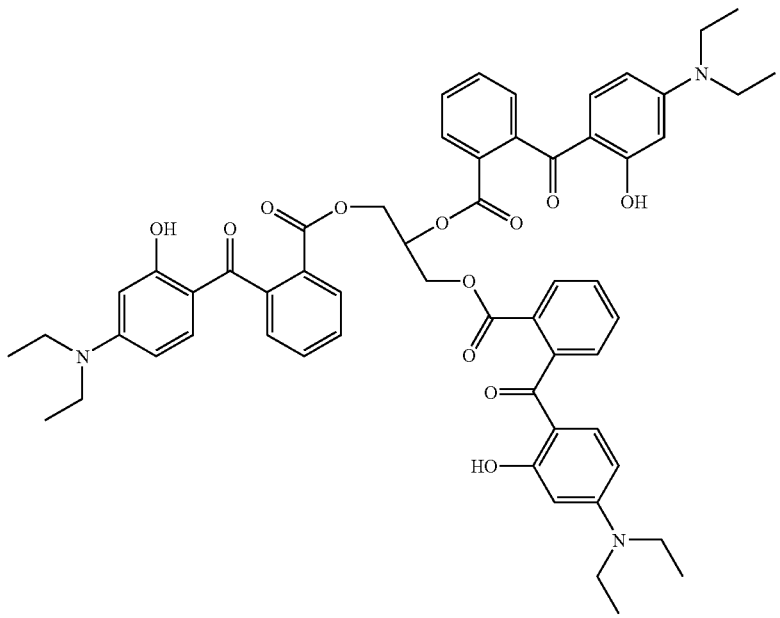 |
| 18 | 117 | 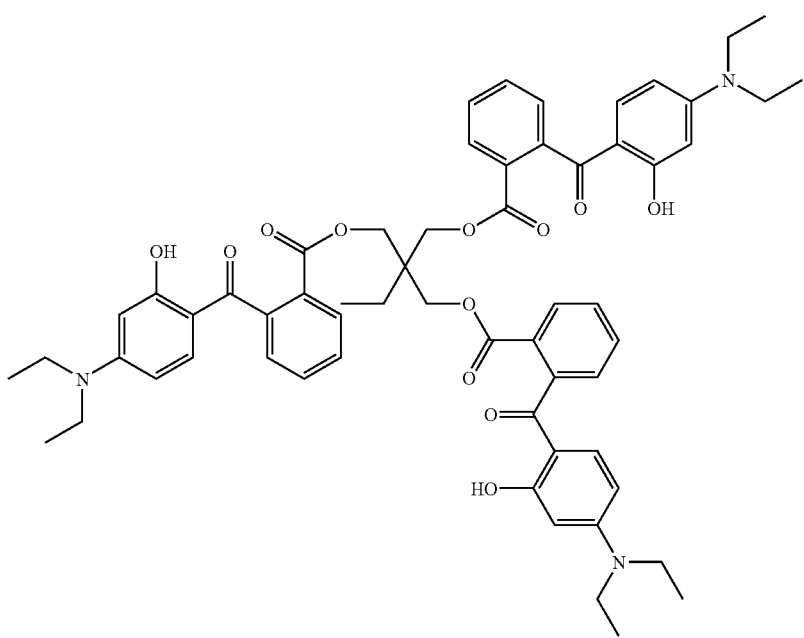 |

| Example | Compound of formula | Structure |
|---|---|---|
| 19 | 118 | 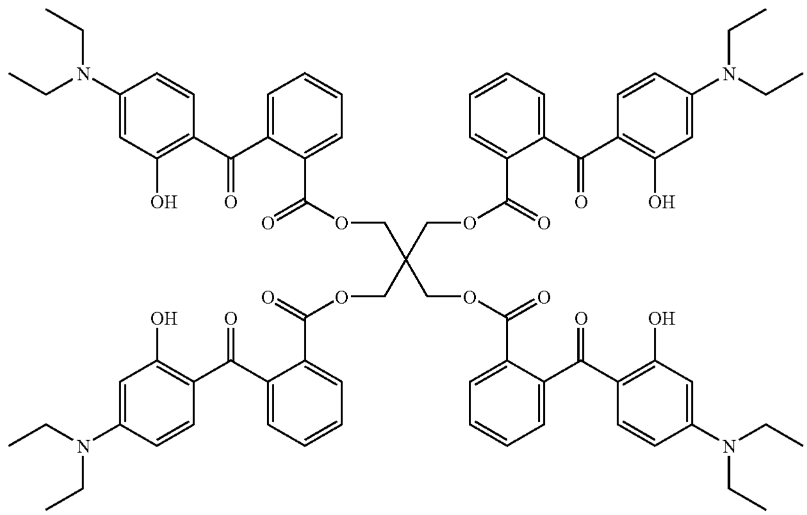 |
| 20 | 119 | 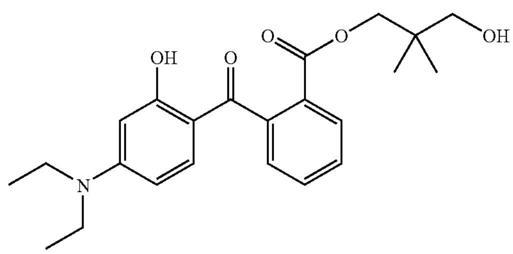 |
| 21 | 120 | 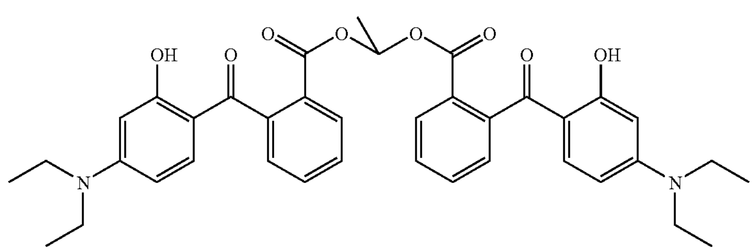 |
| 22 | 121 | 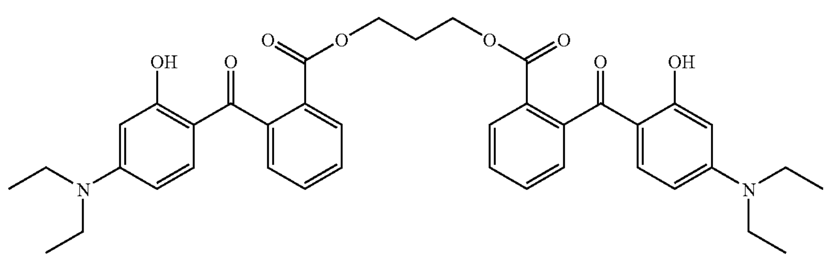 |
| 23 | 122 | 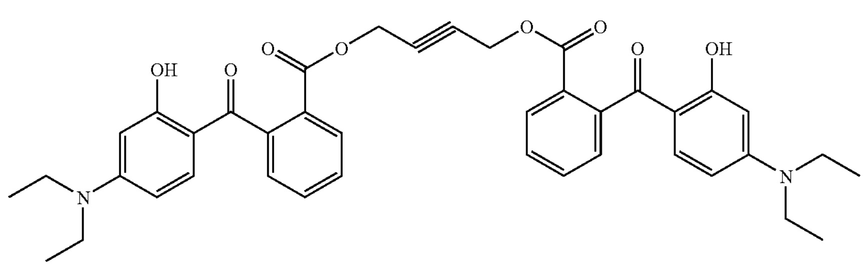 |

APPLICATION EXAMPLES

EXAMPLE 24

Preparation of a Sun Screen Agent

| | |
|---|---|
| Sinnowax AO | 7 g |
| Cerasynt SD-V | 2 g |
| Cetylalcohol | 1.5 g |
| Dow Corning 200 Fluid | 1 g |
| Witconol TN | 15 g |
| Compound of formula (110) | 2 g |
| Octyl Triazone | 2 g |
| Butyl Methoxydibenzoylmethane | 1.5 g |
| Glycerin | 10 g |
| EDTA | 0.2 g |
| Preservative/water deion. | Exp. 100 g |

EXAMPLE 25

Preparation of a Sunscreen Formulation

| | |
|---|---|
| SINNOWAX AO | 7 g |
| Cerasynt SD-V | 2 g |
| Cetylalcohol | 1.5 g |
| Dow Corning 200 Fluid Witconol | 1 g |
| Witconol TN | 15 g |
| Octyl Triazone | 2 g |
| Butyl Methoxydibenzoylmethane | 2 g |
| Parsol 1789 (Hoffman-La Roche) | 1.5 g |
| Glycerin | 10 g |
| Compound of formula (111) | 2 g |
| Preservative/Water deion. | Exp. 100 g |

EXAMPLE 26

Preparation of a Sunscreen Formulation

| | |
|---|---|
| Arlacel 165 FL | 2 g |
| Stearylalcohol | 1 g |
| Stearine TP | 2.5 g |
| Dow Corning 200 Fluid | 0.5 g |
| Witconol TN | 15 g |
| Triethanolamin | 0.5 g |
| Compound of formula (111) | 1.5 g |
| Octyl Triazone | 2 g |
| Butyl Methoxydibenzoylmethane | 1 g |
| Glycerine | 5 g |
| Amphisol K | 1 g |
| Synhalen K | 0.3 g |
| Methocel F4M EDTA | 0.1 g |
| Triethanolamine | 0.2 g |
| Preservative/waterer deion. | auf pH = 7 exp. 100 g |

EXAMPLE 27

O/W Emulsion

| (A): | |
|---|---|
| Compound of formula (110) or (111) | 3 g |
| Sesame Oil | 10 g |
| Glyceryl Stearate | 4 g |
| Stearic Acid | 1 g |
| Cetyl Alcohol | 0.5 g |
| Polysorbate 20 | 0.2 g |
| (B): | |
| Propylene Glycol | 4 g |
| Propylparabene | 0.05 g |
| Methylparabene | 0.15 g |
| Triethanolamine | 0.1 g |
| Carbomer 934 | 0.1 g |
| Water | ad 100 ml |

Preparation of the Emulsion

Phase (A):

Firstly, the UV absorber is dissolved in sesame oil. The other components of (A) are added thereto and combined.

Phase (B):

Propylparabene and methylparabene are dissolved in propylene glycol. 60 ml of water are then added, heating to 70° C. is carried out and then carbomer 934 is emulsified therein.

Emulsion:

(A) is slowly added to (B) with vigorous application of mechanical energy. The volume is adjusted to 100 ml by the addition of water.

EXAMPLE 28

Daily Care Cream, Type O/W

| | INCI name | % w/w (as used) |
|---|---|---|
| Part A | Glyceryl stearate (and) cetearyl alcohol (and) cetyl palmitate (and) cocoglycerides | 4.0 |
| | Ceteareth-12 | 4.0 |
| | Cetearyl alcohol | 2.0 |
| | Dicaprylyl ether | 4.5 |
| | Ethylhexyl stearate | 4.0 |
| | Hexyl laurate | 3.5 |
| | Ethylhexyl triazone | 1.0 |
| | Benzylidene malonate polysiloxane | 2.0 |
| | HDI/trimethylol hexyl-lactone crosspolymer (and) silica | 5.0 |
| | Stearyl dimethicone | 1.0 |
| | Dimethicone | 2.0 |
| | Cetyl alcohol | 0.8 |
| | Compound of formula (110) or (111) | 2.0 |
| Part B | Water | q.s. to 100 |
| | Water (and) scleroglucan (and) phenoxyethanol | 2.0 |
| | Glycerol | 2.0 |
| Part C | Steareth-10 allyl ether/acrylate copolymer | 0.45 |
| | Phenoxyethanol (and) methylparaben (and) ethylparaben (and) butylparaben (and) propylparaben (and) isobutylparaben | 0.7 |
| Part D | Aqua (and) tocopheryl acetate (and) caprylic/capric triglyceride (and) polysorbate 80 (and) lecithin | 4.0 |
| Part E | Water (and) sodium hydroxide | q.s. |
| | Fragrance | q.s. |

Preparation Procedure:

Part A and part B are heated separately to 80° C. Part A is poured into part B, whilst stirring continuously. Afterwards the mixture is homogenized with an Ultra Turrax at 11 000 rpm for 20 sec. The mixture is cooled to 60° C. and part C is added. At a temperature below 30° C., part D is added and the pH value is adjusted with sodium hydroxide to between 6.5 and 7.0. Finally, fragrance is added.

EXAMPLE 29

Sun-Protection Cream, Type O/W

|  | INCI name | % w/w (as used) |
|---|---|---|
| Part A | Polyglyceryl-3 methylglucose distearate | 2.0 |
|  | Decyl oleate | 5.7 |
|  | Isopropyl palmitate | 5.8 |
|  | Caprylic/capric triglyceride | 6.5 |
|  | Compound of formula (110) or (111) | 2.0 |
|  | Ethylhexyl methoxycinnamate | 5.0 |
|  | Cetyl alcohol | 0.7 |
| Part B | Glycerol | 3.0 |
|  | Carbomer | 0.3 |
|  | Water | q.s. to 100 |
| Part C | Phenoxyethanol (and) methylparabene (and) ethylparabene (and) butylparabene (and) propylparabene (and) isobutylparabene | 0.5 |
| Part D | 2,2'-Methylene-bis-(6-(2H-benzotriazole-2-yl)-4-(1,1,3,3-tetramethylbutyl)-phenol (Tinosorb M) (and) aqua (and) decyl glucoside (and) propylene glycol (and) xanthan gum | 8.0 |
|  | Water | 20.0 |
| Part E | Water (and) sodium hydroxide | q.s. |
|  | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. The mixture is cooled to 60° C. and part C and part D are incorporated. The mixture is homogenised again for a short time (5 sec./11 000 rpm) and further cooled, with moderate stirring. At room temperature, the pH is adjusted with sodium hydroxide solution to between 5.5 and 6.0. Finally, fragrance is added.

EXAMPLE 30

Daily Care UV-Protection Lotion

|  | INCI name | % w/w (as used) |
|---|---|---|
| Part A | Oleth-3 phosphate | 0.6 |
|  | Steareth-21 | 2.5 |
|  | Steareth-2 | 1.0 |
|  | Cetyl alcohol | 0.8 |
|  | Stearyl alcohol | 1.5 |
|  | Tribehenin | 0.8 |
|  | Isohexadecane | 8.0 |
|  | Compound of formula (110) or (111) | 5.0 |
| Part B | Water | q.s. to 100 |
|  | Glycerol | 2.0 |
|  | 2,2'-Methylene-bis-(6-(2H-benzotrizole-2-yl)-4-(1,1,3,3- tetramethylbutyl)-phenol (Tinosorb M) (and) aqua (and) decyl glucoside (and) propylene glycol (and) xanthan gum | 3.0 |
|  | Disodium EDTA | 0.1 |
| Part C | Water | 20.0 |
|  | Diazolidinyl urea (and) iodopropynyl butylcarbamate | 0.15 |
|  | Propylene glycol | 4.0 |
| Part D | Sodium acrylate copolymer (and) liquid paraffin (and) PPG-1 trideceth-6 | 1.5 |
|  | Cyclopentasiloxane | 4.5 |
|  | PEG-12 dimethicone | 2.0 |
|  | Tocopheryl acetate | 0.45 |
|  | Water (and) citric acid | q.s. |
| Part E | Fragrance | q.s. |

Preparation Procedure

Heat part A and part B separately to 75° C. Pour part A into part B, whilst stirring continuously. Immediately after emulsification, incorporate in the mixture SF 1202 and SF 1288 from part D. Afterwards homogenise with an Ultra Turrax at 11 000 rpm for 30 sec. Allow to cool to 65° C. and incorporate SALCARE™ SC91. At a temperature below 50° C., add part C. At 35° C. or below, incorporate vitamin E acetate and subsequently adjust the pH with citric acid. At room temperature, add part E.

EXAMPLE 31

Sun-Protection Cream, Type O/W

|  | INCI name | % w/w (as used) |
|---|---|---|
| Part A | Polyglyceryl-3 methylglucose distearate | 2.0 |
|  | Decyl oleate | 5.7 |
|  | Isopropyl palmitate | 5.8 |
|  | Caprylic/capric triglyceride | 6.5 |
|  | Compound of formula (110) or (111) | 2.0 |
|  | Ethylhexyl methoxycinnamate | 5.0 |
|  | Cetyl alcohol | 0.7 |
| Part B | Glycerol | 3.0 |
|  | Carbomer | 0.3 |
|  | Water | q.s. to 100 |
| Part C | Phenoxyethanol (and) methylparabene (and) ethylparabene (and) butylparabene (and) propylparabene (and) isobutylparabene | 0.5 |
| Part D | 2,2'-Methylene-bis-(6-(2H-benzotriazole-2-yl)-4-(1,1,3,3-tetramethylbutyl)-phenol (and) aqua (and) decyl glucoside (and) propylene glycol (and) xanthan gum | 8.0 |
|  | Water | 20.0 |
| Part E | Water (and) sodium hydroxide | q.s. |
|  | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. The mixture is cooled to 60° C., and part C and part D are incorporated. The mixture is homogenised again for a short time (5 sec./11 000 rpm). After further cooling, with moderate stirring, the pH is adjusted with sodium hydroxide at room temperature. A solution between pH 5.50 and 6.00 is obtained. Finally, fragrance is added.

EXAMPLE 32

Sun-Protection Cream, Type O/W

|  | INCI name | % w/w (as used) |
|---|---|---|
| Part A | Polyglyceryl-3 methylglucose distearate | 2.0 |
|  | Decyl oleate | 5.7 |
|  | Isopropyl palmitate | 5.8 |
|  | Caprylic/capric triglyceride | 6.5 |
|  | Mixture of the Compound of formula (110) or (111) (50%) and Uvinul A Plus CAS Reg. No. 302776-68-7 (50%) | 2.0 |
|  | Ethylhexyl methoxycinnamate | 5.0 |
|  | Cetyl alcohol | 0.7 |
| Part B | Glycerol | 3.0 |
|  | Carbomer | 0.3 |
|  | Water | q.s. to 100 |
| Part C | Phenoxyethanol (and) methylparabene (and) ethylparabene (and) butylparabene (and) propylparabene (and) isobutylparabene | 0.5 |
| Part D | 2,2'-Methylene-bis-(6-(2H-benzotriazole-2-yl)-4-(1,1,3,3- tetramethylbutyl)-phenol (and) aqua (and) decyl glucoside (and) propylene glycol (and) xanthan gum | 8.0 |
|  | Water | 20.0 |
| Part E | Water (and) sodium hydroxide | q.s. |
|  | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. After cooling 60° C., part C and part D are incorporated. The mixture is homogenised again for a short time (5 sec./11 000 rpm). After further cooling, with moderate stirring, the pH is adjusted at room temperature with sodium hydroxide solution to between 5.50 and 6.00. Finally, fragrance is added.

What is claimed is:

1. Compound of formula

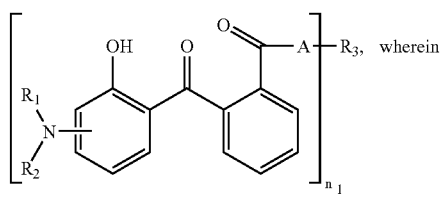

$R_1$ and $R_2$ independently from each other are; $C_1$-$C_{20}$alkyl; $C_2$-$C_{20}$alkenyl; $C_3$-$C_{10}$cycloalkyl; or $C_3$-$C_{10}$cycloalkenyl; or $R_1$ and $R_2$ together with the linking nitrogen atom form a 5- or 6-membered heterocyclic ring;

$n_1$ is a number from 1 to 4;
when $n_1$=1,
$R_3$ is a saturated or unsaturated heterocyclic radical;
when $n_1$ is 2,
$R_3$ is an alkylen-, cycloalkylene, alkenylene or phenylene radical which is optionally substituted by a carbonyl or carboxy group; or a radical of formula *—$CH_2$—C≡C—$CH_2$—*; or $R_3$ together with A forms a bivalent radical of the formula

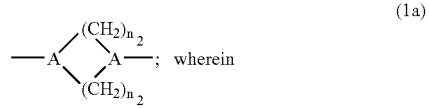

$n_2$ is a number from 1 to 3;
when $n_1$ is 3,
$R_3$ is an alkantriyl radical;
when $n_1$ is 4,
$R_3$ is an alkantetrayl radical;
A is —O—; or —N($R_5$)—; and
$R_5$ is hydrogen; $C_1$-$C_5$alkyl; or hydroxy-$C_1$-$C_5$alkyl.

2. Compound according to claim 1, wherein
$R_1$ and $R_2$ independently from each other are $C_1$-$C_{20}$alkyl; $C_2$-$C_{20}$alkenyl; $C_3$-$C_{10}$cycloalkyl; or $C_3$-$C_{10}$cycloalkenyl; or $R_1$ and $R_2$ together with the linking nitrogen atom form a 5- or 6-membered heterocyclic ring;
$n_1$ is a number from 1 to 4;
when $n_1$ is 1,
$R_3$ is a saturated or unsaturated heterocyclic radical;
when $n_1$ is 2,
$R_3$ is an alkylen-, cycloalkylen- or alkenylene radical which is optionally interrupted by a carbonyl- or carboxy group;
when $n_1$ is 3,
$R_3$ is an alkantriyl radical;
when $n_1$ is 4,
$R_3$ is an alkantetrayl radical;
A is —O—; or —N($R_5$)—; and
$R_5$ is hydrogen; $C_1$-$C_5$alkyl; or hydroxy-$C_1$-$C_5$alkyl.

3. Compound according to claim 1, wherein
$R_1$ and $R_2$ are $C_1$-$C_{20}$alkyl.

4. Compound according to claim 1, wherein
$R_1$ and $R_2$ independently from each other are $C_1$-$C_5$alkyl.

5. Compound according to claim 1, wherein
$R_1$ and $R_2$ in formula (1) have the same definition.

6. Compound according to claim 1, wherein
if $n_1$ is 1,
$R_3$ is a saturated heterocyclic radical.

7. Compound according to claim 6, wherein
$R_3$ is a monocyclic radical of 5, 6 or 7 ring members with one or more hetero atoms.

8. Compound according to claim 7, wherein
$R_3$ is morpholinyl; piperazinyl; piperidyl; pyrazolidinyl; imadazolidinyl; or pyrrolidinyl.

9. Compound according to claim 1, wherein
$R_3$ is an unsaturated heterocyclic radical.

10. Compound according to claim 9, wherein
$R_3$ is a polycyclic radical.

11. Compound according to claim 1, wherein $R_3$ is a radical of formula

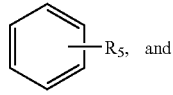 (1a)

$R_5$ is polycyclic heteroaromatic radical with one or 2 heteroatoms.

12. Compound according to claim 11, wherein $R_3$ is a radical of formula

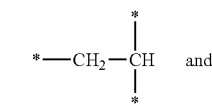 (1b)

$R_6$ is hydrogen; or $C_1$-$C_5$alkyl.

13. Compound according to claim 1, wherein, if $n_1$ is 2, $R_3$ is a $C_1$-$C_{12}$alkylene radical.

14. Compound according to claim 13, wherein $R_3$ is a radical of formula

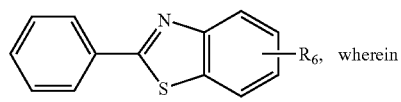

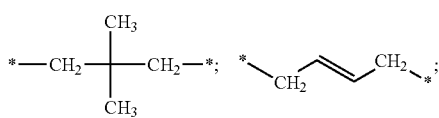

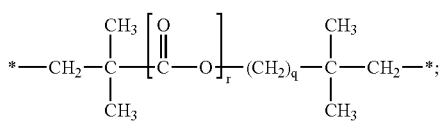

r is 0 or 1; and
q = is a number from 0 to 5.

15. Compound according to claim 1, wherein, when $n_1$ is 3; $R_3$ is a radical of formula

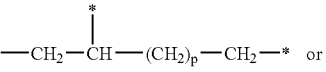 (1a)

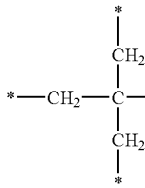 (1b)

p is a number from 0 to 3; and
$R_1$, $R_2$ and A are defined as in formula (1).

16. Compound according to claim 1, wherein, when $n_1$ is 4, $R_3$ is a radical of formula

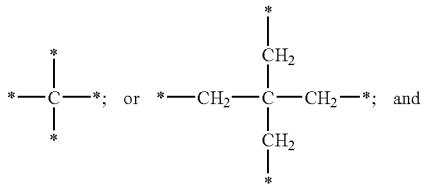

$R_1$, $R_2$ and A are defined as in formula (1).

17. Compound according to claim 1, which corresponds to formula

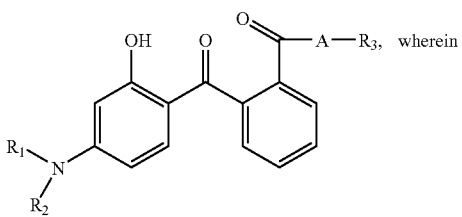 (2)

$R_1$ and $R_2$ independently from each other are $C_1$-$C_5$alkyl;
A is —NH; or —O—; and
$R_3$ is a saturated or unsaturated heterocyclic radical.

18. Compound according to claim 1, which corresponds to formula
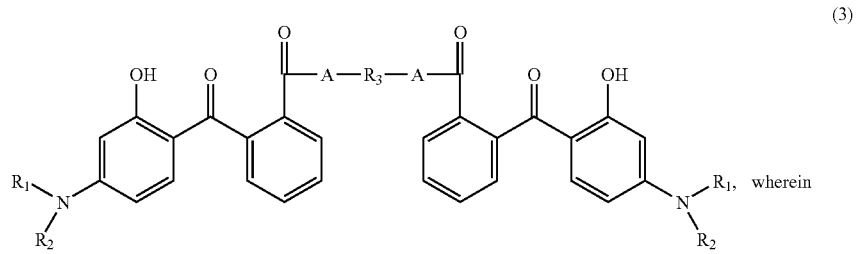
(3)
R$_1$ and R$_2$ independently from each other are C$_1$-C$_5$alkyl;
A is —NH; or —O—; and
R$_3$ is a C$_1$-C$_{12}$alkylene radical.
19. Compound according to claim 1, which corresponds to formula
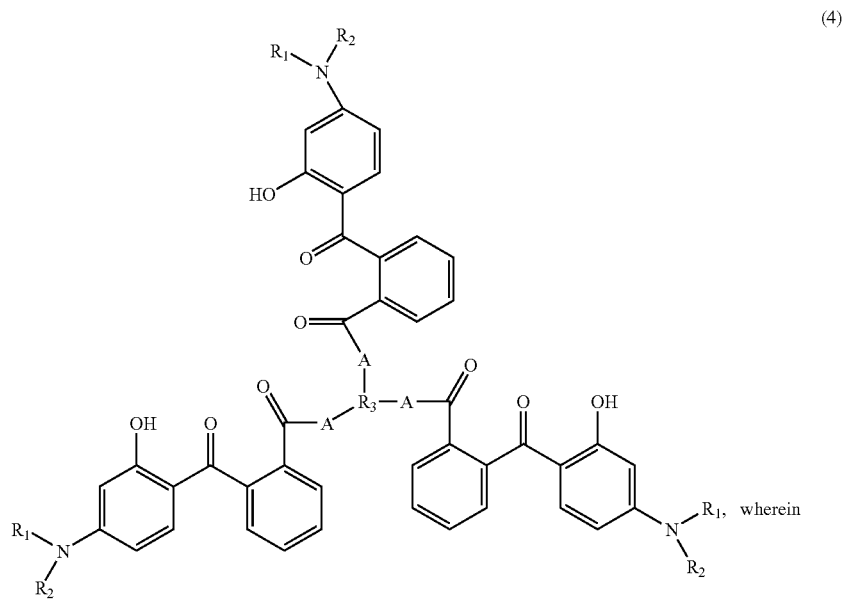
(4)
R$_1$ and R$_2$ independently from each other are C$_1$-C$_5$alkyl;
A is —NH; or —O—; and
R$_3$ is
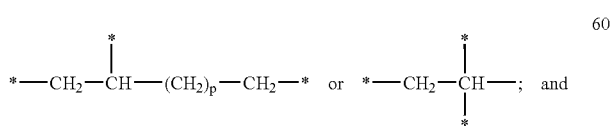
and
p is a number from 0 to 3.

20. Compound according to claim 1, which corresponds to formula

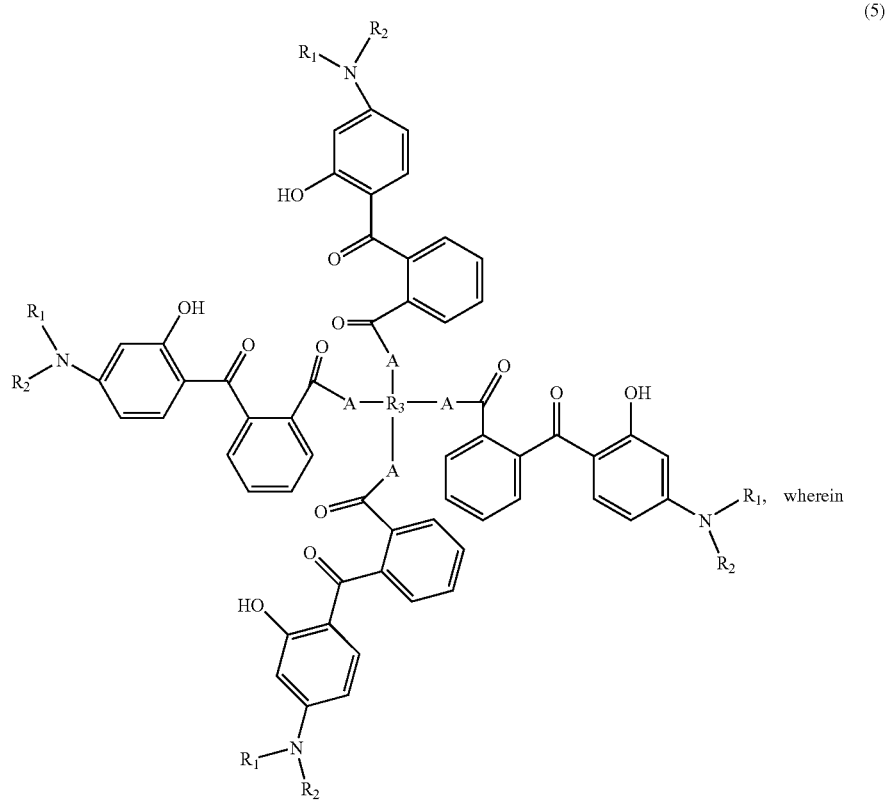

(5)

$R_3$ is a radical of formula

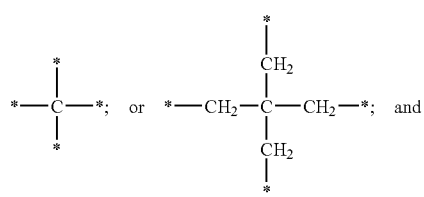

$R_1$, $R_2$ and A are defined as in formula (1).

21. A process for the preparation of the compounds of formula (1), which comprises, dehydrating (a) the compound formula

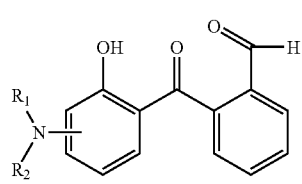

(6a)

to the compound of formula

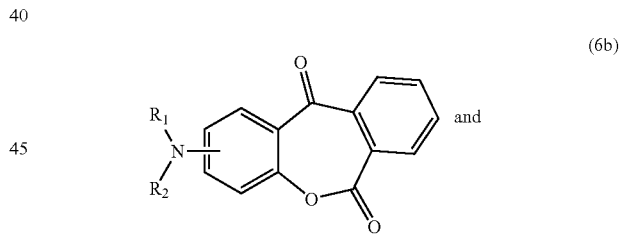

(6b)

(b) reacting the anhydride with the compound of formula (6c$_1$) H—N(R$_5$)—R$_3$ or (6c$_2$) H—O—R$_3$ to the compound of formula

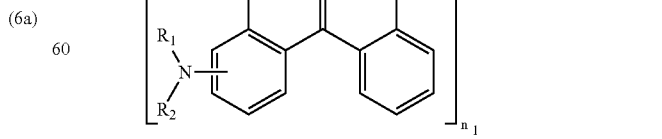

(1')

$R_1$ and $R_2$ independently from each other are hydrogen; $C_1$-$C_{20}$alkyl; $C_2$-$C_{20}$alkenyl; $C_3$-$C_{10}$cycloalkyl; or $C_3$-$C_{10}$cycloalkenyl; or $R_1$ and $R_2$ together with the linking nitrogen atom form a 5- or 6-membered heterocyclic ring;

$n_1$ is 1 to 4;

if $n_1$ is 1, $R_3$ is hydrogen; $C_1$-$C_{20}$alkyl; hydroxy-$C_1$-$C_5$alkyl; $C_2$-$C_{20}$alkenyl; $C_3$-$C_{10}$-Cyclohexyl not substituted or substituted with one or more $C_1$-$C_5$alkyl; $(Y-O)_pZ$; $C_6$-$C_{10}$aryl; or a saturated or unsaturated heterocyclic radical;

Y is $C_1$-$C_{12}$alkylen;

Z is $C_1$-$C_5$alkyl;

p is a number from 1 to 20;

if $n_1$ is 2, $R_3$ is a alkylen-, cycloalkylen- or alkenylene radical which is optionally interrupted by carbonyl- or carboxy group;

if $n_1$ is 3, $R_3$ is an alkantriyl radical;

if $n_1$ is 4, $R_3$ is a alkantetrayl radical;

A is —O—; or —N($R_5$)—;

$R_5$ is hydrogen; $C_1$-$C_5$alkyl; or hydroxy-$C_1$-$C_5$alkyl; and $R_5$ is hydrogen; $C_1$-$C_5$alkyl; or hydroxy-$C_1$-$C_5$alkyl.

22. Process according to claim 21, wherein the process refers to compounds of formula

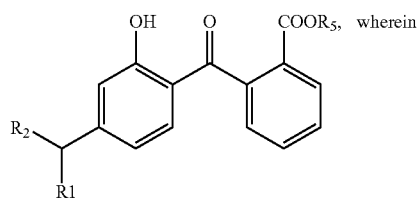
(7)

$R_1$ and $R_2$ independently from each other are $C_1$-$C_{12}$alkyl; and $R_5$ is hydrogen; $C_1$-$C_{12}$alkyl; or $C_3$-$C_6$-cycloalkyl.

23. A cosmetic preparation comprising at least one or more compounds of formula (1) according to claim 1 with cosmetically acceptable carriers or adjuvants.

24. Compounds of formula

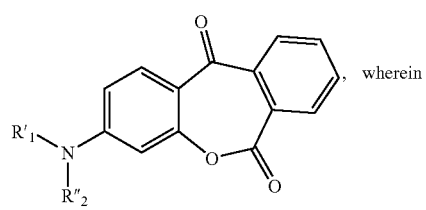
(6b′), wherein $R_1'$ and $R_2''$ independently from each other are hydrogen; $C_1$-$C_{20}$alkyl; $C_2$-$C_{20}$alkenyl; $C_3$-$C_{10}$-cycloalkyl; or $C_3$-$C_{10}$cycloalkenyl; or $R_1$ and $R_2$ together with the linking nitrogen atom form a 5- or 6-membered heterocyclic ring.

25. UV-Absorber-dispersion, comprising (a) a micronised UV absorber of formula

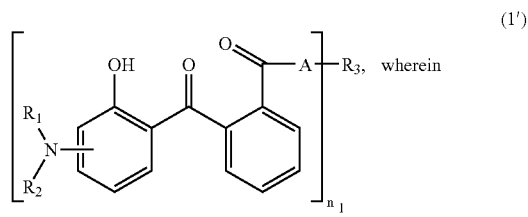
(1′)

$R_1$ and $R_2$ independently from each other are hydrogen; $C_1$-$C_{20}$alkyl; $C_2$-$C_{20}$alkenyl; $C_3$-$C_{10}$cycloalkyl; or $C_3$-$C_{10}$cycloalkenyl; or $R_1$ and $R_2$ together with the linking nitrogen atom form a 5- or 6-membered heterocyclic ring;

when $n_1$ is 1, $R_3$ is hydroxy-$C_1$-$C_5$alkyl; $C_2$-$C_{20}$alkenyl; $(Y-O)_p Z$; $C_6$-$C_{10}$aryl; or a saturated or unsaturated heterocyclic radical;

Y $C_1$-$C_{12}$alkylen;

Z $C_1$-$C_5$alkyl;

p is a number from 1 to 20;

when $n_1$ is 2, $R_3$ is a alkylen-, cycloalkylen- or alkenylen- radical optionally interrupted by a carbonyl- or carboxy group;

if $n_1$ is 3, $R_3$ is an alkantriyl radical;

if $n_1$ is 4, $R_3$ is an alkantetrayl radical;

A is —O—; or —N($R_5$)—; and $R_5$ is hydrogen; $C_1$-$C_5$alkyl; or hydroxy —$C_1$-$C_5$alkyl;

having a particle size from 0.02 to 2 μm, and (b) a suitable dispersing agent.

26. A cosmetic preparation according to claim 23, wherein the compounds of formula (1) are present in micronized form.

* * * * *